(12) United States Patent
Penders et al.

(10) Patent No.: US 10,499,844 B2
(45) Date of Patent: Dec. 10, 2019

(54) SYSTEMS AND METHODS FOR HEALTH MONITORING

(71) Applicants: Julien Penders, San Francisco, CA (US); Eric Dy, San Francisco, CA (US)

(72) Inventors: Julien Penders, San Francisco, CA (US); Eric Dy, San Francisco, CA (US)

(73) Assignee: Bloom Technologies NV, Diepenbeek (BE)

( * ) Notice: Subject to any disclaimer, the term of this patent is extended or adjusted under 35 U.S.C. 154(b) by 51 days.

(21) Appl. No.: 15/200,500

(22) Filed: Jul. 1, 2016

(65) Prior Publication Data
US 2018/0000405 A1    Jan. 4, 2018

(51) Int. Cl.
*A61B 5/00*    (2006.01)
*A61B 5/0205*    (2006.01)
(Continued)

(52) U.S. Cl.
CPC .......... *A61B 5/4362* (2013.01); *A61B 5/0002* (2013.01); *A61B 5/0075* (2013.01);
(Continued)

(58) Field of Classification Search
CPC ... A61B 5/4362; A61B 5/0002; A61B 5/0075; A61B 5/00205; A61B 5/00444;
(Continued)

(56) References Cited

U.S. PATENT DOCUMENTS

| | | | |
|---|---|---|---|
| 5,623,939 | A | 4/1997 | Garfield et al. |
| 5,776,073 | A | 7/1998 | Garfield et al. |

(Continued)

FOREIGN PATENT DOCUMENTS

| | | | |
|---|---|---|---|
| CA | 2608497 A1 | 8/2006 |
| CA | 2754721 A1 | 9/2010 |

(Continued)

OTHER PUBLICATIONS

Supplementary European Search Report dated Feb. 17, 2017 for EP 14834450.0, 7 pgs.

(Continued)

*Primary Examiner* — Scott Luan
(74) *Attorney, Agent, or Firm* — Aurora Consulting LLC; Ashley Sloat

(57) ABSTRACT

A system for monitoring health parameters of a user includes a housing including: a plurality of sensors disposed on an outer surface of the housing or within the housing for measuring a plurality of parameters of interest; a processor disposed in the housing and communicatively coupled to the plurality of sensors; a coupling element on the housing for coupling the housing to an accessory; and an accessory identifier positioned on or within the housing and communicatively coupled to the processor. In some embodiments, the housing is reversibly transitionable between an uncoupled state and a coupled state with the accessory. In the coupled state, the accessory identifier senses a type of accessory and the processor activates a subset of the plurality of sensors to measure a subset of the plurality of parameters of interest. In some embodiments, the user is a pregnant female and a fetus developing in the pregnant female.

23 Claims, 18 Drawing Sheets

(51) Int. Cl.

| | | |
|---|---|---|
| *A61B 5/0444* | (2006.01) | |
| *A61B 5/11* | (2006.01) | |
| *A61B 8/08* | (2006.01) | |
| *A61B 7/02* | (2006.01) | |
| *A61B 5/16* | (2006.01) | |
| *A61B 5/145* | (2006.01) | |
| *A61B 5/1468* | (2006.01) | |
| *A61B 7/00* | (2006.01) | |
| *A61B 8/00* | (2006.01) | |
| *A61B 5/08* | (2006.01) | |
| *A61B 5/024* | (2006.01) | |
| *A61B 5/053* | (2006.01) | |

(52) U.S. Cl.
CPC ........ *A61B 5/02055* (2013.01); *A61B 5/0444* (2013.01); *A61B 5/1118* (2013.01); *A61B 5/14539* (2013.01); *A61B 5/14542* (2013.01); *A61B 5/165* (2013.01); *A61B 5/4356* (2013.01); *A61B 5/4815* (2013.01); *A61B 5/6804* (2013.01); *A61B 7/00* (2013.01); *A61B 7/02* (2013.01); *A61B 8/0866* (2013.01); *A61B 8/4227* (2013.01); *A61B 8/4416* (2013.01); *A61B 8/4472* (2013.01); *A61B 5/02405* (2013.01); *A61B 5/02411* (2013.01); *A61B 5/02438* (2013.01); *A61B 5/053* (2013.01); *A61B 5/0816* (2013.01); *A61B 5/1468* (2013.01); *A61B 2503/02* (2013.01); *A61B 2503/045* (2013.01); *A61B 2560/045* (2013.01)

(58) Field of Classification Search
CPC .............. A61B 5/1118; A61B 5/14539; A61B 5/14542; A61B 5/1468; A61B 5/165; A61B 5/4356; A61B 5/4815
See application file for complete search history.

(56) References Cited

U.S. PATENT DOCUMENTS

| | | | |
|---|---|---|---|
| 5,954,663 | A | 9/1999 | Gat |
| 6,134,466 | A | 10/2000 | Rosenberg |
| 6,816,744 | B2 | 11/2004 | Garfield et al. |
| 7,532,923 | B1 | 5/2009 | Hayes-Gill et al. |
| 8,116,855 | B2 | 2/2012 | James et al. |
| 8,229,550 | B2 | 7/2012 | James et al. |
| 8,255,238 | B2 | 8/2012 | Powell et al. |
| D717,674 | S | 11/2014 | Vu et al. |
| 8,880,140 | B2 | 11/2014 | Hayes-Gill et al. |
| D739,284 | S | 9/2015 | Vu et al. |
| D739,775 | S | 9/2015 | Vu et al. |
| D739,776 | S | 9/2015 | Vu et al. |
| D739,777 | S | 9/2015 | Vu et al. |
| D739,778 | S | 9/2015 | Vu et al. |
| D740,706 | S | 10/2015 | Vu et al. |
| D743,819 | S | 11/2015 | Golnik et al. |
| D752,764 | S | 3/2016 | Peters |
| 9,307,923 | B2 | 4/2016 | Peters et al. |
| 9,314,203 | B2 | 4/2016 | Peters |
| 9,392,952 | B1 | 7/2016 | Oz et al. |
| 9,572,504 | B2 | 2/2017 | Oz et al. |
| 9,642,544 | B2 | 5/2017 | Oz et al. |
| 9,713,430 | B2 | 7/2017 | Oz et al. |
| 9,763,583 | B2 | 9/2017 | Oz et al. |
| 2005/0267376 | A1* | 12/2005 | Marossero ......... A61B 5/02411 600/511 |
| 2007/0191728 | A1 | 8/2007 | Shennib |
| 2007/0255184 | A1 | 11/2007 | Shennib |
| 2008/0029333 | A1 | 2/2008 | Oz |
| 2008/0275316 | A1 | 11/2008 | Fink et al. |
| 2009/0143650 | A1 | 6/2009 | Guion-Johnson et al. |
| 2009/0192396 | A1 | 7/2009 | Hayes-Gill et al. |
| 2009/0299212 | A1 | 12/2009 | Principe et al. |
| 2010/0235782 | A1 | 9/2010 | Powell et al. |
| 2010/0274145 | A1 | 10/2010 | Tupin, Jr. et al. |
| 2011/0190652 | A1 | 8/2011 | Fink et al. |
| 2011/0237972 | A1 | 9/2011 | Garfield et al. |
| 2011/0251512 | A1 | 10/2011 | Fink et al. |
| 2011/0251817 | A1 | 10/2011 | Burns et al. |
| 2011/0270118 | A1 | 11/2011 | Garfield et al. |
| 2011/0306893 | A1 | 12/2011 | Harrold et al. |
| 2012/0075103 | A1 | 3/2012 | Powell et al. |
| 2012/0150010 | A1 | 6/2012 | Hayes-Gill et al. |
| 2012/0232398 | A1 | 9/2012 | Roham et al. |
| 2012/0265090 | A1 | 10/2012 | Fink et al. |
| 2013/0030831 | A1 | 1/2013 | Powell et al. |
| 2013/0090538 | A1 | 4/2013 | Garfield et al. |
| 2013/0275152 | A1 | 10/2013 | Moore et al. |
| 2014/0180169 | A1 | 6/2014 | Peters et al. |
| 2014/0249436 | A1 | 9/2014 | Serguei et al. |
| 2015/0004912 | A1 | 1/2015 | Diamond et al. |
| 2015/0022366 | A1 | 1/2015 | Vu et al. |
| 2015/0105646 | A1 | 4/2015 | Peters |
| 2016/0058363 | A1 | 3/2016 | Hayes-Gill et al. |
| 2016/0066827 | A1 | 3/2016 | Workman et al. |
| 2016/0103590 | A1 | 4/2016 | Vu et al. |
| 2016/0139787 | A1* | 5/2016 | Joo .......................... G09G 5/14 715/765 |
| 2016/0157717 | A1 | 6/2016 | Gaster et al. |
| 2016/0256132 | A1 | 9/2016 | VandeLaar et al. |
| 2017/0156594 | A1* | 6/2017 | Stivoric .............. A61B 5/7275 |
| 2017/0224268 | A1* | 8/2017 | Altini .................. A61B 5/4356 |

FOREIGN PATENT DOCUMENTS

| | | |
|---|---|---|
| CA | 2765124 A1 | 12/2010 |
| CA | 2870560 A1 | 10/2013 |
| EP | 1220640 B1 | 5/2008 |
| EP | 1941830 A2 | 7/2008 |
| EP | 1941832 A1 | 7/2008 |
| EP | 1680018 B1 | 11/2008 |
| EP | 2451345 A2 | 1/2011 |
| EP | 1952760 B1 | 4/2012 |
| EP | 2745774 A1 | 6/2014 |
| EP | 3011464 A1 | 12/2014 |
| EP | 2862511 A1 | 4/2015 |
| EP | 2328471 B1 | 9/2015 |
| EP | 2997892 A1 | 3/2016 |
| WO | 2005110236 A1 | 11/2005 |
| WO | 2009150440 A1 | 12/2009 |
| WO | 2010105063 A1 | 9/2010 |
| WO | 2010144413 A1 | 12/2010 |
| WO | 2011004147 A2 | 1/2011 |
| WO | 2011094609 A2 | 8/2011 |
| WO | 2011119757 A2 | 9/2011 |
| WO | 2011130291 A2 | 10/2011 |
| WO | 2011130295 A2 | 10/2011 |
| WO | 2012061827 A1 | 5/2012 |
| WO | 2012131171 A1 | 10/2012 |
| WO | 2012142241 A2 | 10/2012 |
| WO | 2013052612 A2 | 4/2013 |
| WO | 2013158625 A1 | 10/2013 |
| WO | 2014035836 A1 | 3/2014 |
| WO | 2014162135 A1 | 10/2014 |
| WO | 2014205201 A1 | 12/2014 |
| WO | 2015013163 A1 | 1/2015 |
| WO | 2015020886 A1 | 2/2015 |
| WO | 2015056027 A1 | 4/2015 |
| WO | 2016131630 A1 | 8/2016 |

OTHER PUBLICATIONS

Dovetail Care, "Pregnansi", SimilarWeb Ltd, 2016, 7 pages.

Shulgin et al., "Electrohysterographic Signals Processing for Uterine Activity Detection ad Characterization", IEEE XXXIV International Scientific Conference Electronics and Nanotechnology, 2014, pp. 269-272.

Horoba, et al., "Statistical Approach to Analysis of Electrohysterographic Signal", Proceedings of the First Joint BMES/EMBS Conference, Atlanta, GA, 1999, pp. 887.

(56) References Cited

OTHER PUBLICATIONS

International Search Report dated Dec. 24, 2014 from International Application PCT/US2014/049280, 4 pgs.
Written Opinion of International Search Report dated Dec. 24, 2014 from International Application PCT/US2014/049280, 15 pgs.
De Lau Hinke et al., "Towards improving uterine electrical activity modeling and electrohysterography: ultrasonic quantification of uterine movements during labor.", Nordic Federation of Societies of Obstetrics and Gynecology, Acta Obstetricia et Gynecologica Scandinavica, 2013, 1323-1326, 92 (11).
Zimmer et al., "The relationship between uterine contractions, fetal movements and fetal heart rate patterns in the active phase of labor", Elsevier Science Publishers B.V. (Biomedical Division), 1987, 89-95, 25 (2).
International Search Report dated May 6, 2016 from International Application PCT/IB2015/002194, 7 pgs.
Written Opinion of International Search Report dated May 6, 2016 from International Application PCT/IB2015/002194, 11 pgs.
European Search Report and Written Opinon of European Search Report for Belgium National Application BE201505056, 18 pgs.
Written Opinion of International Search Report dated Dec. 19, 2018 from International Application PCT/IB2018/055394, 12 pgs.
International Search Report dated Dec. 19, 2018 from International Application PCT/IB2018/055394, 8 pgs.
Lange, L. et al. "Velocity and Directionality of the Electrohysterographic Signal Propagation," Plos One, vol. 9, No. 1, Jan 21, 2014, pp. 1-6.
Maner, W. et al. "Identification of Human Term and Preterm Labor using Artificial Neural Networks on Uterine Electromyography Data," Annuals of Biomedical Engineering, Kluwer Academic Publishers—Plem Publishers, NE, vol. 35, No. 3, Jan. 17, 2007, pp. 465-473.
Penders, J. et al. "Wearable Sensors for Healthier Pregnancies," IEEE, Proceedings of the IEEE, 2015, http://www.ieee.org/publications_standards/publications/rights/index.html.
U.S. Appl. No. 14/909,739, filed Feb. 2, 2016, Wireless Pregnancy Monitor.

* cited by examiner

SYSTEMS AND METHODS FOR HEALTH MONITORING

TECHNICAL FIELD

This disclosure relates generally to the field of health monitoring, and more specifically to the field of digital health monitoring. Described herein are systems, devices, and methods for health monitoring one or more individuals through various life stages.

BACKGROUND

Health prior to conception, during pregnancy, and post-partum for both partners is critical. Body weight, nutrition, stress, exercise, and caffeine intake can affect each of these stages. For example, these factors may affect a woman and man's ability to contribute to conception, a woman's health during pregnancy, a man's ability to manage stress during pregnancy, and a woman and man's ability to manage post-partum stress and hormonal changes. Further, a similar set of factors can affect fetal wellbeing in utero and newborn health post-partum. Recent research has shown that the time from conception through the first two years of life will determine the health of a child, the ability to learn in school, and/or to perform in a future job (Thurow, Roger. 2006. "The First 1,000 Days.").

Current systems for health monitoring focus on monitoring the mom or fetus during pregnancy. For example, available systems monitor maternal uterine activity, and/or maternal and fetal heart rate in the hospital. In some instances, these systems are particularly suited for pregnant females with a high body-mass index. Current systems for at home use measure maternal activity, maternal sleep, or maternal weight.

Pregnancy monitoring solutions targeted to the consumer focus on monitoring a few parameters, for instance maternal health, fetal kicks, or contractions. However, these systems fail to provide a comprehensive solution to all the needs of a woman during pregnancy. These systems fail to adapt to the changing needs of a soon-to-be mom as she is progressing through her pregnancy and parenting experience.

Further, current systems for newborn monitoring are dedicated to measuring newborn heart rate, respiration, or newborn oxygen saturation. However, these currently available systems for pregnancy or newborn monitoring fail to monitor wellbeing of both parents pre-conception, both parents and the fetus during pregnancy, and both parents and the newborn post-partum. Further, monitoring both parents and the baby during all of these stages would be expensive since several unique sensing systems and/or accessories would be required.

SUMMARY

There is a need for new and useful systems and methods for health monitoring. In particular, there is a need for systems, devices, and methods that monitor wellbeing, for example during the first 1000 days of life, of: both parents pre-conception, both parents and the fetus during pregnancy, and/or both parents and the newborn post-partum. The present disclosure provides embodiments that address one or more of these needs.

One aspect of the present disclosure is directed to a modular system for monitoring health parameters of a user. In some embodiments, the modular system includes: a housing including a plurality of sensors disposed on an outer surface of the housing or within the housing for measuring a plurality of parameters of interest; a processor disposed in the housing and communicatively coupled to the plurality of sensors; a coupling element on the housing for coupling the housing to an accessory; and an accessory identifier positioned on the housing and communicatively coupled to the processor. In some embodiments, the housing is reversibly transitionable between an uncoupled state and a coupled state with the accessory. In some embodiments, in the coupled state, the accessory identifier senses a type of accessory and the processor activates a subset of the plurality of sensors to measure a subset of the plurality of parameters of interest.

In some embodiments, the subset of the plurality of parameters of interest measured changes based on the type of accessory coupled to the housing.

In some embodiments, the accessory identifier comprises a plurality of electrical terminals. In some embodiments, in the coupled state, the plurality of electrical terminals is connected to a plurality of electrical receptacles on the accessory, such that an impedance between the plurality of electrical receptacles is detectable by the accessory identifier.

In some embodiments, the outer surface of the housing includes a first surface and a second surface. In some embodiments, the first surface is a user facing surface and the second surface is an accessory facing surface. In some embodiments, the second surface includes the coupling element and/or accessory identifier. In some embodiments, the first surface includes the accessory identifier. In some embodiments, an outer perimeter of the housing includes the coupling element.

In some embodiments, the system further includes the accessory. In some embodiments, the accessory is one or more of wearable by a user and positionable proximate a user. In some embodiments, the accessory includes an aperture, defined by a plurality of sidewalls, for receiving the housing. In some embodiments, the accessory includes a base sized, shaped, and configured for receiving the housing. In some embodiments, the accessory includes one or more electrical contacts or conductive materials for transmitting signals and/or measuring one or more parameters of interest through the base of the accessory.

In some embodiments, the type of accessory is one of a wristband, a bra clip, a first trimester belly patch, a second trimester belly patch, a third trimester belly patch, a pregnancy support belt, a patch coupled to baby clothing, and an accessory integrated into clothing.

In some embodiments, the system further includes an antenna and transceiver communicatively coupled to the processor, wherein the antenna and transceiver wirelessly transmit the subset of the plurality of parameters of interest to a computing device.

In some embodiments, the subset of the plurality of parameters of interest are displayable to a user on a display of the computing device. In some embodiments, a graphical user interface displayed on the display of the computing device adapts based on the type of accessory identified.

In some embodiments, the plurality of sensors includes one or more of: a physiological sensor, a bio-potential sensor, an activity sensor, an optical sensor, a bio-impedance sensor, an acoustic sensor, an ultrasound sensor, an electrochemical sensor, a near-infrared spectroscopy sensor, and a temperature sensor.

In some embodiments, during pre-conception, the plurality of sensors measure one of: a paternal subset of the plurality of parameters of interest and a maternal subset of the plurality of parameters of interest. In some embodiments, the paternal subset of the plurality of parameters of interest include one or more of: an activity level, a sleep quality, a stress level, an oxygen saturation level, a cardiorespiratory fitness level, a heart rate, and a heart rate variability. In some embodiments, the maternal subset of the plurality of parameters of interest include one or more of: an activity level, a sleep quality, a stress level, an oxygen saturation level, a cardiorespiratory fitness level, a heart rate, and a heart rate variability.

In some embodiments, during pregnancy, the plurality of sensors measures a maternal subset of the plurality of parameters of interest and a fetal subset of the plurality of parameters of interest. In some embodiments, the maternal subset of the plurality of parameters of interest include one or more of: an electrohysterography signal, maternal uterine activity, maternal uterine contractions, maternal heart electrical activity, maternal heart rate, maternal heart rate variability, a maternal activity level, a maternal sleep quality, a maternal oxygen saturation level, a maternal cardiorespiratory fitness level, and a maternal stress level. In some embodiments, the fetal subset of the plurality of parameters of interest include one or more of: fetal movement, fetal heart electrical activity, fetal heart sound, fetal heart rate, fetal heart rate variability, an amount of amniotic fluid, placental oxygenation, placental temperature, placental pH, fetal breathing, fetal position, fetal orientation, and fetal distress.

In some embodiments, during post-partum, the plurality of sensors measures one of: a maternal subset of the plurality of parameters of interest, a newborn subset of the plurality of parameters of interest, and a paternal subset of the plurality of parameters of interest. In some embodiments, the maternal subset of the plurality of parameters of interest include one or more of: an activity level, a sleep quality, stress level, an oxygen saturation level, a cardiorespiratory fitness level, heart rate, and heart rate variability. In some embodiments, the newborn subset of the plurality of parameters of interest include one or more of: a heart rate, heart rate variability, blood oxygenation level, breathing rate, movement, temperature, and vocal sounds. In some embodiments, the paternal subset of the plurality of parameters of interest include one or more of: an activity level, a sleep quality, a stress level, an oxygen saturation level, a cardiorespiratory fitness level, a heart rate, and a heart rate variability.

In some embodiments, the modular system is configured for use with a plurality of users and to identify each of the plurality of users based on an identification of the accessory coupled to the housing.

Another aspect of the present disclosure is directed to a system for measuring health parameters of a user. In some embodiments, the system includes a plurality of sensors for measuring a plurality of parameters of interest of a user; a coupling element for coupling the system to an accessory worn by a user or positionable proximate the user; and a processor communicatively coupled to the plurality of sensors. In some embodiments, the processor analyzes a plurality of sensor outputs from the plurality of sensors and automatically determines a type of the accessory coupled to the system based on the analyzed plurality of sensor outputs.

In some embodiments, the plurality of parameters of interest of the user includes one or more of: a maternal activity level, maternal sleep quality, maternal stress level, maternal oxygen saturation level, maternal cardiorespiratory fitness level, maternal heart rate, maternal heart rate variability, maternal electrohysterography signal, maternal uterine activity, maternal uterine contractions, maternal heart electrical activity, paternal activity level, paternal sleep quality, paternal stress level, paternal oxygen saturation level, paternal cardiorespiratory fitness level, paternal heart rate, paternal heart rate variability, paternal heart electrical activity, fetal movement, fetal heart electrical activity, fetal heart sound, fetal heartbeat, fetal heart rate, fetal heart rate variability, an amount of amniotic fluid, placental oxygenation, placental temperature, placental pH, fetal breathing, fetal position, fetal orientation, fetal distress, fetal breathing movement, newborn heart rate, newborn blood oxygenation level, newborn breathing rate, newborn movement, newborn temperature, and newborn vocal sounds.

DETAILED DESCRIPTION

Figure 1:
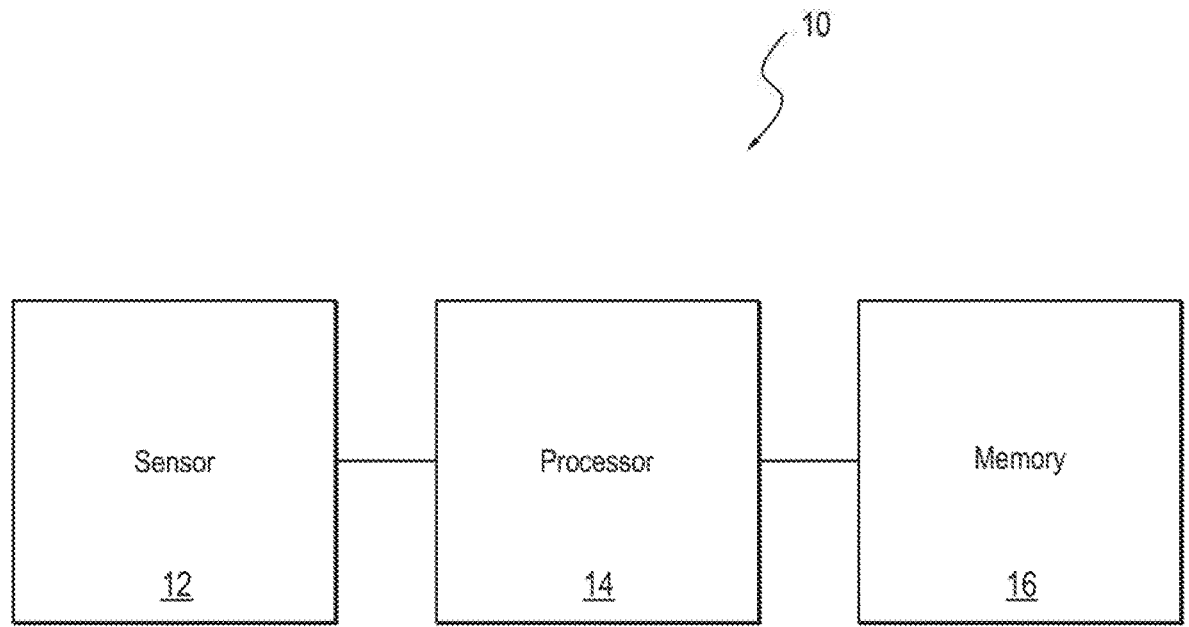
FIG. 1 illustrates one embodiment of a sensing module.

The foregoing is a summary, and thus, necessarily limited in detail. The above mentioned aspects, as well as other aspects, features, and advantages of the present technology will now be described in connection with various embodiments. The inclusion of the following embodiments is not intended to limit the invention to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure. Disclosed herein are systems and methods for health monitoring.

In general, the systems and methods described herein include a sensing module and accessory used to monitor health parameters of a user. A user includes a parent (e.g., mother, father, step-mother, step-father, etc.), male pre-conception, female pre-conception, pregnant female, expectant mother, fetus, female post-partum, male post-partum (i.e., after woman gives birth to newborn), newborn, baby, toddler, physician, healthcare provider, doula, nurse practitioner, midwife, veterinarian, obstetrician, gynecologist, pediatrician, friend, family member, spouse, partner, sibling, or any other individual, group, or community involved in pre-conception, pregnancy, and/or post-partum care and planning. The system may be used for couples trying to conceive, for expecting couples, and/or for new parents.

As used herein, "pregnant woman" and "pregnant female" may be used interchangeably. It will be appreciated by one skilled in the art that each of the embodiments described herein may be used to monitor health parameters of any pregnant mammal regardless of species.

As used herein, "mother" and "female" may be used interchangeably. It will be appreciated by one skilled in the art that each of the embodiments described herein may be used to monitor health parameters of any egg-producing mammal regardless of species.

As used herein, "father" and "male" may be used interchangeably. It will be appreciated by one skilled in the art that each of the embodiments described herein may be used to monitor health parameters of any sperm-producing mammal regardless of species.

As used herein, "newborn" and "baby" may be used interchangeably. It will be appreciated by one skilled in the art that each of the embodiments described herein may be used to monitor health parameters of any newly born or recently born mammal regardless of species.

In some embodiments, more than one user may use the system at the same time or substantially the same time. For example, in some embodiments, the wellbeing of a fetus and the woman carrying the fetus may be simultaneously or substantially simultaneously monitored. In some such embodiments, a kick count, heart rate, and an amount or level of amniotic fluid of the developing fetus may be measured while a stress level, heart rate, and activity level of the woman carrying the developing fetus is measured.

In some embodiments, each user may be using or wearing a different accessory coupled to a sensing module for health monitoring. In one non-limiting example, a male pre-conception may monitor one or more health parameters and a female pre-conception may monitor one or more health parameters to increase likelihood and/or efficiency of conception. In another non-limiting example, a pregnant female may be monitoring one or more health parameters of herself and her fetus while a physician or healthcare provider is also viewing and/or monitoring the one or more health parameters of the pregnant female and the fetus. In another non-limiting example, one or more health parameters of a newborn may be monitored while the mother and father are also monitored post-partum.

As used herein, "accessory" refers to any garment, device, jewelry, decoration, or adornment used or worn by a user. For example, in some variations, an accessory includes any wearable item: a watchband or wristband (FIGS. 6A-6B), bracelet, bra clip (FIGS. 7A-7B), cufflink, patch (FIGS. 8A-8B, FIGS. 9A-9B) (e.g., patch on a belly region, back region, wrist region, or neck region); a first trimester belly patch (FIGS. 8A-8B), second trimester belly patch (FIGS. 8A-8B), or third trimester belly patch (FIGS. 9A-9B); etc.), pregnancy support belt, headband, anklet, hat (FIG. 10B), onesie (FIG. 10A), sleeper, pocket in a piece of clothing, patch on a piece of clothing, scarf, or any other type of accessory or clothing. In some embodiments, one or more system components are integrated into a garment or clothing, for example bra, t-shirt, pants, underwear, etc. In some variations, an accessory includes any item that is positionable in proximity to a user, for example on or in a sleeping surface (e.g., bed, crib, etc.), on or in a stuffed animal or other object near the user, on a computing device, in the same room as the user, carried by a user, etc. In one non-limiting example, a sensing module may be coupled to or positioned in a mattress in a crib or bed for monitoring a newborn in the crib or bed (e.g., sleep quality, movement, breathing or crying sounds, etc.). In another non-limiting example, the sensing module may include a sound level meter positionable proximate the newborn (e.g., on the mattress, in the crib, in the room, etc.) or carried with the newborn (e.g., in a stroller, car seat, diaper bag, etc.) for detecting and/or measuring a newborn's cries, breathing sounds, or other audible noises. In another non-limiting example, the sensing module (e.g., comprising an accelerometer) may be positioned on the bed proximate the mother and/or father to measure a sleep quality of the mother and/or father. In some embodiments, the accessory has dual functionality such that it can either be worn by the user or positioned proximate the user to measure one or more health parameters of the user.

In some embodiments, the accessory is reusable; in other embodiments, the accessory is disposable. For example, in some embodiments, a patch may comprise a disposable material such as acrylate, a synthetic material, hydrogel, or silicone. In one embodiment, a patch may comprise silicone. A reusable and/or disposable material may provide complete freedom and/or flexibility of use for the user. For example, the user may elect to move the patch to another location depending on the time of day (e.g., night vs. day), activities occurring at a point in time (e.g., showering, sleeping, exercising, etc.), or based on one or more observations (e.g., reduced kick count, increase heart rate, poor sleep quality, etc.).

Systems

As shown in FIG. 1, in various embodiments, a system 10 for monitoring health parameters of a user includes at least a sensor 12 in electrical communication with a processor 14 and a computer-readable medium (i.e., memory) 16. FIG. 1 illustrates a functional block diagram, and it is to be appreciated that the various functional blocks of the depicted system need not be separate structural elements. For example, in some embodiments, the processor 14 and memory 16 may be embodied in a single chip or two or more chips.

The sensor or a plurality of sensors 12 function to measure a plurality of parameters of interest. For example, a sensor 12 may detect movement (e.g., maternal and/or paternal physical activity, fetal kicks, fetal position, etc.), events (e.g., fetal kicks, contraction, etc.), physiological features (e.g., heart rate, placental oxygenation level, etc.) and/or changes in the environment (e.g., an amount of amniotic fluid) and provide a corresponding output or signal. In some embodiments, the system includes one sensor 12; in some embodiments, the system includes a plurality of sensors 12. For example, the sensor 12 may include one or more sensors configured to measure a plurality of parameters of interest including: a maternal activity level, maternal sleep quality, maternal stress level, maternal heart rate, maternal heart rate variability, maternal electrohysterography signal, maternal uterine activity, maternal uterine contractions, maternal heart electrical activity, maternal oxygen saturation level, maternal cardiorespiratory fitness level, paternal activity level, paternal sleep quality, paternal stress level, paternal heart rate, paternal heart rate variability, paternal heart electrical activity, paternal oxygen saturation level, paternal cardiorespiratory fitness level, fetal movement, fetal heart electrical activity, fetal heart sound, fetal heart beat, fetal heart rate, fetal heart rate variability, an amount of amniotic fluid, placental oxygenation, placental temperature, placental pH, fetal breathing, fetal position, fetal orientation, fetal distress, fetal breathing movement, newborn heart rate, newborn blood oxygenation level, newborn breathing rate, newborn movement, newborn temperature, and newborn vocal sounds.

In some embodiments, the sensor 12 is coupled to, embedded in, or otherwise disposed on a housing, which is configured for coupling to an accessory worn by a user. For example, the housing comprising the sensor is configured for placement on an outer surface of a female's, male's, and/or baby's body. In some embodiments, the sensor is configured for positioning proximate the user. For example, the housing comprising the sensor is configured for placement on a surface near a user, placement in the same room as a user, carrying by a user, or otherwise unattached to the user, as described elsewhere herein.

The sensor 12 may include a physiological sensor, a biopotential sensor, an inertial sensor, an acoustic sensor, an ultrasound sensor, a bio-impedance sensor, an optical sensor, a near-infrared spectroscopy sensor, an electrochemical sensor, and/or a temperature sensor. A biopotential sensor interacts with ionic charge carriers in or at the surface of the body and transduces ionic electrical potentials into electric currents read by a processor.

A physiological sensor may include one or more sensors configured to measure an electrohysterography (EHG) signal, maternal uterine activity, maternal uterine muscle contractions, maternal heart electrical activity, maternal heart rate, fetal movement, fetal heart rate, maternal activity, maternal stress, and/or fetal stress. The one or more physiological sensors may sense one or more biopotential signals. In one non-limiting embodiment, the physiological sensor includes an EHG sensor and an electrocardiogram (ECG) sensor.

A biopotential sensor as described herein may include at least one measurement electrode and at least one reference electrode. In some configurations, one reference electrode and a plurality of measurement electrodes are present in the biopotential sensor. A biopotential sensor may measure an ECG, electroencephalogram (EEG) or electromyogram (EMG) of the fetus or expectant mother.

An inertial sensor as described herein includes one or more accelerometers, gyroscopes, global positioning system (GPS) receivers, and/or magnetometers to measure a specific force (i.e., g-force or mass-specific force), angular rate, and/or magnetic field surrounding the body. For example, an inertial sensor of the system may be used to measure paternal activity level, maternal activity level, fetal movement, fetal kicks, fetal position, and/or fetal orientation.

An acoustic sensor as described herein uses acoustic waves propagated through a portion of the abdomen (may include a portion of the uterus and/or fetus) of the user (e.g., pregnant woman) to measure characteristics of the user (e.g., pregnant women, uterus, placenta, fetus, or any other characteristic of the fetus or structure supporting the growth of the fetus). As the acoustic waves propagate through the abdomen, one or more characteristics of the waves change, for example in velocity, amplitude, etc. These changes are sensed by the sensor and output as a sensor signal. In some variations, the acoustic sensor is a passive sensor, such that the acoustic waves are autonomously generated by the body of the pregnant mom or the fetus. In some other variations, the acoustic sensor is an active sensor, such that the acoustic waves are generated externally using an acoustic wave generator.

An ultrasound sensor as described elsewherein uses ultrasonic waves propagated through a portion of the abdomen (e.g., may include a portion of the uterus and/or fetus) of user (e.g., pregnant women) to measure characteristics of the user (e.g., pregnant women, uterus, placenta, fetus, or any other characteristic of the fetus or structure supporting the growth of the fetus). As the ultrasonic waves propagate through the abdomen, one or more characteristics of the waves change, for example in velocity, amplitude, frequency, etc. These changes are sensed by the sensor and output as a sensor signal.

A bio-impedance sensor as described herein uses electrical current to measure, for example a variety of cardiac parameters of the mother pre-conception, father pre-conception, pregnant female, fetus, mother post-partum, father post-partum, and/or newborn. The cardiac parameters may include stroke volume, heart rate, cardiac output, heart rate variability, or any other parameter known to one of skill in the relevant art. In some embodiments, one or more bio-impedance sensors are used to measure an amount of amniotic fluid. For example, an excessive accumulation of amniotic fluid (i.e., polyhydramnios) or a deficiency in amniotic fluid (i.e., oligohydramnios) may be detected by one or more bio-impedance sensors. One non-limiting example of a bio-impedance sensor includes an impedance plethysmography sensor.

An optical sensor as described herein illuminates one or more areas of the skin and measures changes in light absorption or reflection. For example, an optical sensor may be used to measure oxygen saturation of the placenta, blood flow to various organs or appendages (e.g., of the mother, father, fetus, and/or newborn), blood pressure (e.g., of the mother, father, fetus, and/or newborn), or pulse (e.g., of the mother, father, fetus, and/or newborn). One non-limiting example of an optical sensor includes a photoplethysmogram.

A near-infrared spectroscopy sensor as described herein uses near-infrared light to illuminate one or more areas of the skin and measure changes in electromagnetic absorption in this specific band. It may be used non-invasively to assess placental function, for example by measuring placental oxygenation, blood flow, sugar level, or pH, and/or health of the mother pre-conception or during pregnancy, for example blood flow, sugar level, or pH.

An electrochemical sensor as described herein uses electrochemical reactions to measure the concentrations of specific ions, and may be used to measure the acidity or pH of body fluids such as sweat, interstitial fluid, and/or blood.

A temperature sensor as described herein may be used to sense or measure a change in temperature, an average body temperature, and/or a placental temperature. Non-limiting examples of temperature sensors include a thermistor and a thermocouple.

Returning to FIG. 1, a system 10 for health monitoring may further include a processor 14. The processor may be a general purpose microprocessor, a digital signal processor (DSP), a field programmable gate array (FPGA), an application specific integrated circuit (ASIC), or other programmable logic device, or other discrete computer-executable components designed to perform the functions described herein. The processor 14 may also be formed of a combination of computing devices, for example, a DSP and a microprocessor, a plurality of microprocessors, one or more microprocessors in conjunction with a DSP core, or any other suitable configuration.

In some embodiments, the processor 14 is coupled, via one or more buses, to the memory 16 in order to read information from, and optionally write information to, the memory 16. The memory 16 may be any suitable computer-readable medium that stores computer-readable instructions for execution by a processor 14. For example, the computer-readable medium may include one or more of RAM, ROM, flash memory, EEPROM, a hard disk drive, a solid state drive, or any other suitable device. In some embodiments, the computer-readable instructions include software stored in a non-transitory format. The software may be programmed into the memory or downloaded as an application onto the memory. The software may include instructions for running an operating system and/or one or more programs or applications, as described elsewhere herein. When executed by the processor 14, the programs or applications may cause the processor 14 to perform a method of monitoring health parameters of a user. Some such methods are described in more detail elsewhere herein.

Figure 2A:
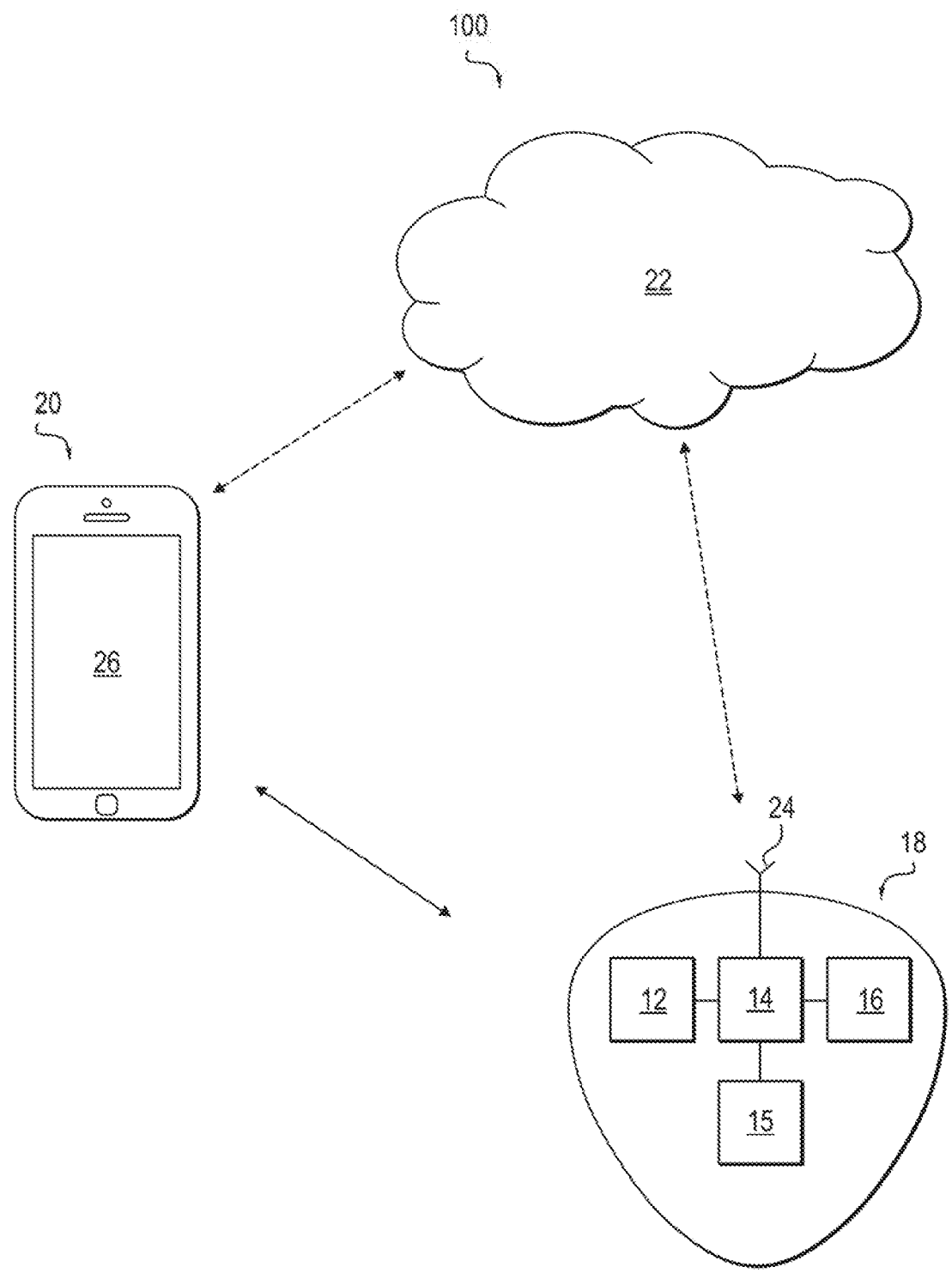
FIG. 2A illustrates one embodiment of a system for health monitoring.
Figure 2B:
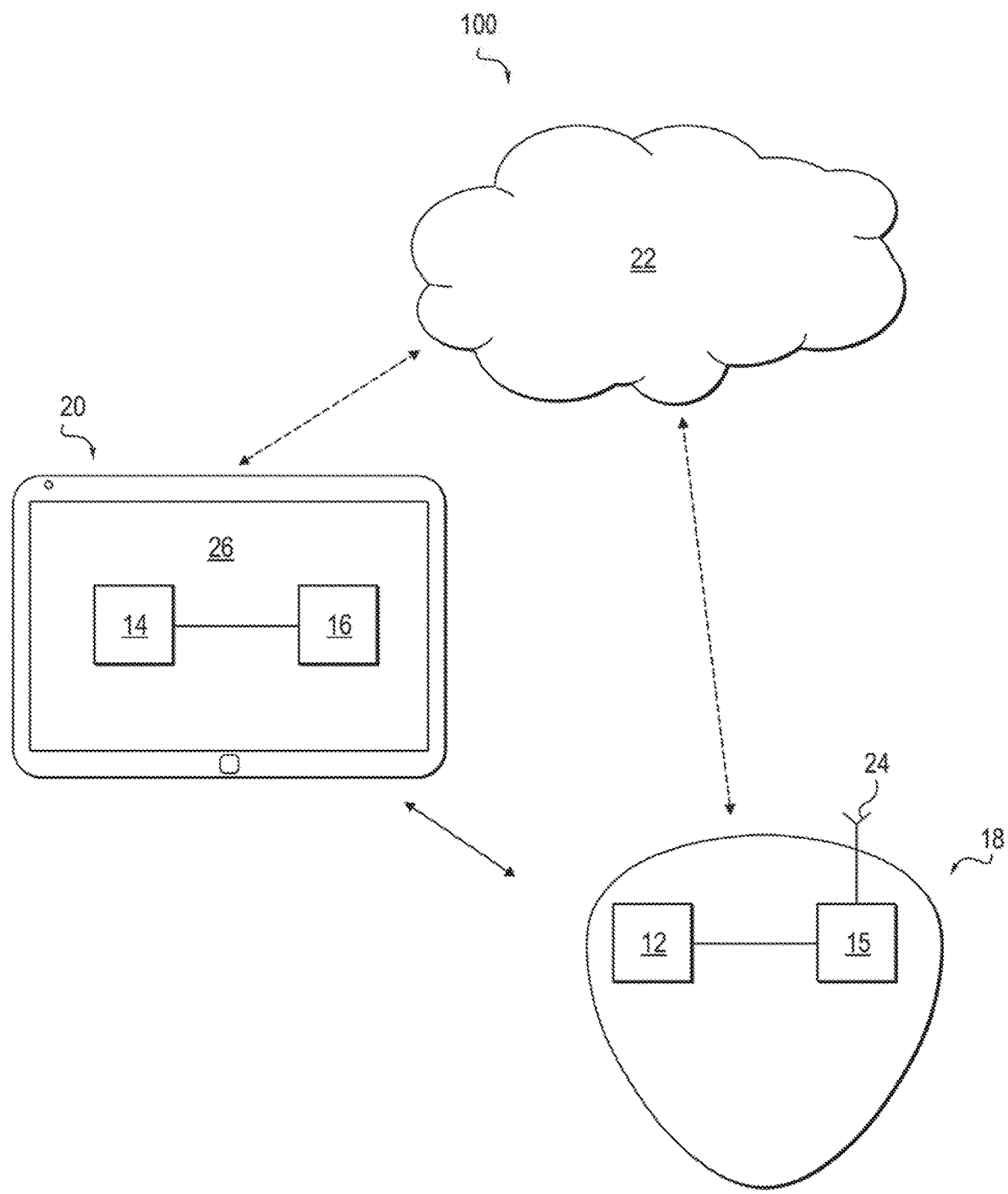
FIG. 2B illustrates one embodiment of a system for health monitoring.
Figure 2C:
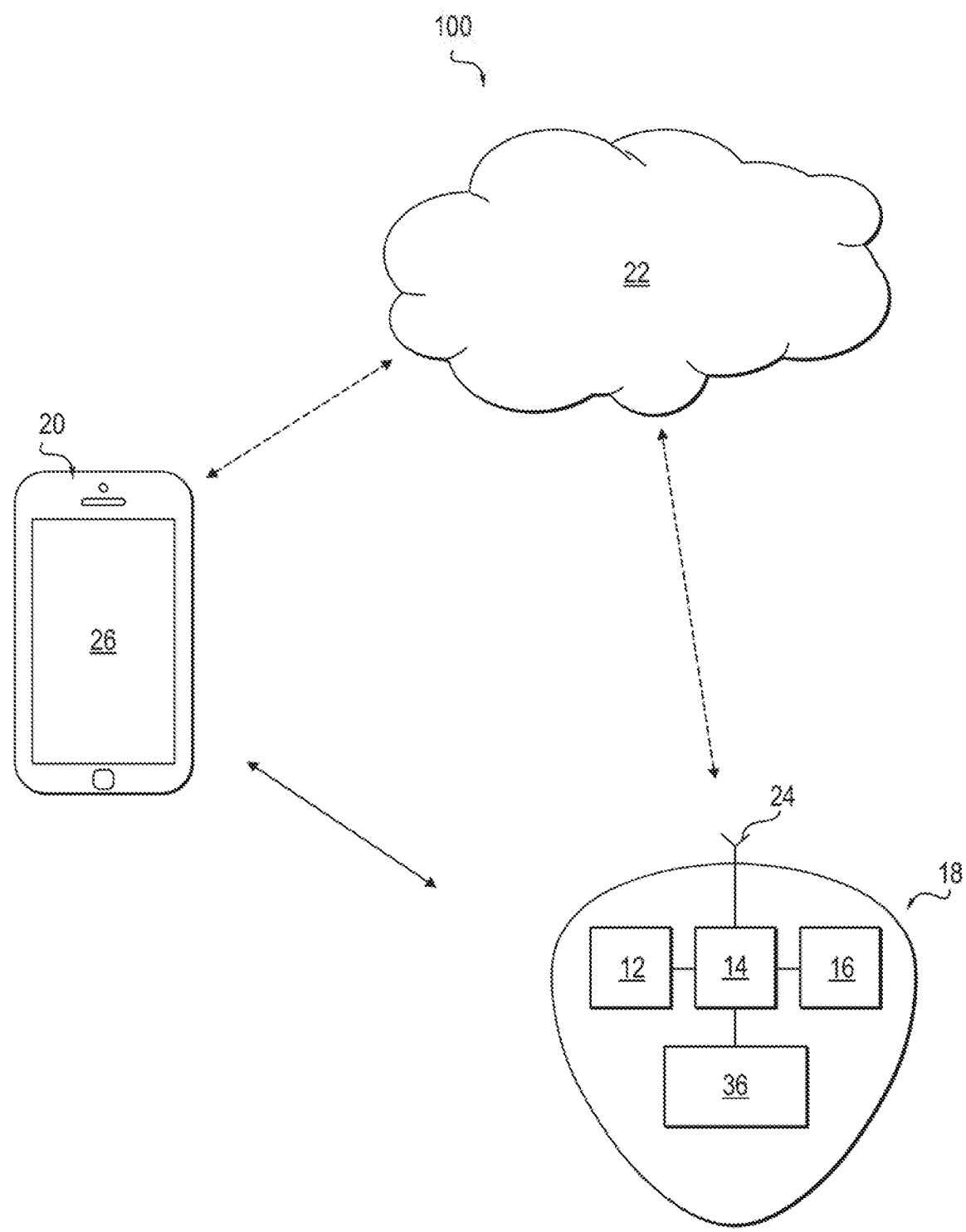
FIG. 2C illustrates one embodiment of a system for health monitoring.
Figure 3A:
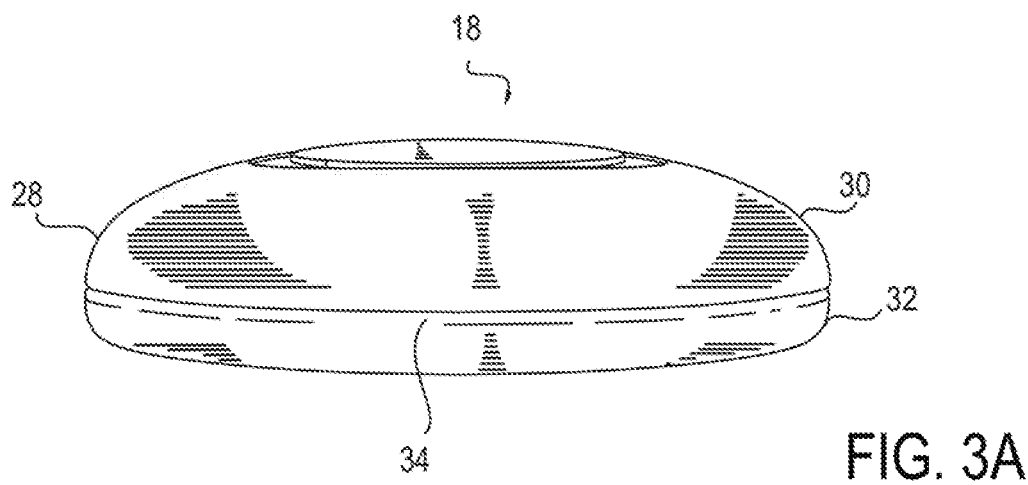
FIG. 3A illustrates one embodiment of a housing comprising a sensing module.

As shown in FIGS. 2A-2C, the system 100 may further include a sensing module 18 and a computing device 20 (e.g., mobile or stationary). As described herein, the sensing module 18 includes a housing (as shown in FIG. 3A) comprising one or more system components (e.g., sensor, processor, memory, electrical circuit, antenna, receiver, transmitter, transceiver, accessory identifier, etc.). In some embodiments, the system 100 also includes a server 22. In some embodiments, such as the embodiment of FIG. 2A, the sensor 12, processor 14, and memory 16 are each positioned on or in the housing of the sensing module 18. An electronic circuit 15 and wireless antenna 24 may also be provided on or in the housing. In such embodiments, signals are: sensed by the sensor 12; amplified, filtered, digitized and/or otherwise processed by the electronic circuit 15; and further processed and analyzed by the processor 14. Execution of instructions stored in memory 16 causes the processor 14 of the sensing module 18 to perform one or more of the methods of monitoring health parameters of a user described elsewhere herein. Analyzed data may be transmitted via the antenna 24 to one or both of the computing device 20 and the server 22 for visual and/or audio presentation to a user, additional analysis, and/or storage.

In other embodiments, such as the embodiment of FIG. 2B, the sensor 12 is positioned on or in the housing of the sensing module 18 with the electronic circuit 15 and wireless antenna 24, while a computing device 20 houses both the processor 14 that performs a method of monitoring a health status of a user and the memory 16 that stores instructions for performing the method. In such embodiments, signals are sensed by the sensor 12 and amplified, filtered, digitized and/or otherwise processed by the electronic circuit 15, and the processed signals are transmitted via the antenna to the computing device. The processor 14 of the computing device 20 analyzes the processed signals and detects and/or monitors health parameters of a user, as described elsewhere herein. The analyzed data may be saved, shared with contacts, or presented to a user via the computing device 20. In some such embodiments, some of or all the analyzed data may be transmitted from the computing device 20 to a server 22 for storage.

In some embodiments, the electronic circuit 15 includes an operational amplifier, a low-pass, high-pass, or band-pass filter, an analog-to-digital (AD) converter, and/or other signal processing circuit components configured to amplify, filter, digitize, and/or otherwise process the sensor signals. The electronic circuit 15 may additionally include a power supply or power storage device, such as a battery or capacitor to provide power to the other electronic components. For example, the electronic circuit 15 may include a rechargeable (e.g., lithium ion) or disposable (e.g., alkaline) battery.

In some embodiments, the antenna 24 includes one or both of a receiver and a transmitter. The receiver receives and demodulates data received over a communication network. The transmitter prepares data according to one or more network standards and transmits data over a communication network. In some embodiments, a transceiver antenna acts as both a receiver and a transmitter for bi-directional wireless communication. As an addition or alternative to the antenna, in some embodiments, a databus is provided within the sensing module 18 so that data can be sent from, or received by, the sensing module 18 via a wired connection.

In some embodiments, there is one-way or two-way communication between the sensing module 18 and the computing device 20, the sensing module 18 and the server 22, and/or the computing device 20 and the server 22. The sensing module 18, computing device 20, and/or server 22 may communicate wirelessly using Bluetooth, low energy Bluetooth, near-field communication, infrared, WLAN, Wi-Fi, CDMA, LTE, other cellular protocol, other radiofrequency, or another wireless protocol. Additionally or alternatively, sending or transmitting information between the sensing module 18, the computing device 20, and the server 22 may occur via a wired connection such as IEEE 1394, Thunderbolt, Lightning, DVI, HDMI, Serial, Universal Serial Bus, Parallel, Ethernet, Coaxial, VGA, or PS/2.

In some embodiments, the computing device 20 is a computational device wrapped in a chassis that includes a visual display 26 with or without touch responsive capabilities (e.g., Thin Film Transistor liquid crystal display (LCD), in-place switching LCD, resistive touchscreen LCD, capacitive touchscreen LCD, organic light emitting diode (LED), Active-Matrix organic LED (AMOLED), Super AMOLED, Retina display, Haptic/Tactile touchscreen, or Gorilla Glass), an audio output (e.g., speakers), an audio input (e.g., microphone), a central processing unit (e.g., processor or microprocessor), internal storage (e.g., flash drive), n number of components (e.g., specialized chips and/or sensors), and/or n number of radios (e.g., WLAN, LTE, WiFi, Bluetooth, GPS, etc.).

In some embodiments, the computing device 20 is a mobile computing device, for example a mobile phone, smartphone, smart watch, smart glasses, smart contact lenses, other wearable computing device, tablet, laptop, netbook, notebook, or any other type of mobile computing device. In some embodiments, the computing device 20 is a stationary computing device, for example a personal computer, workstation, desktop computer, or other stationary computing device.

In some embodiments, the server 22 is a database server, application server, Internet server, or other remote server. In some embodiments, the server 22 may store user profile data, historical user data, historical community data, algorithms, machine learning models, software updates, or other data. The server 22 may share this data with the computing device 20 or the sensing module 18, and the server 22 may receive newly acquired user data from the sensing module 18 and/or the computing device 20.

In some embodiments, the computing device 20 includes an application downloaded onto and/or stored in memory 16. The application may be used by any user of the system 100. For example, upon detecting which user is using the system 100 (e.g., by user input, device identification, system sensing which accessory is being used, etc.), the application may automatically update, change, or display content specific for or tailored to the user, or otherwise modify to better measure, monitor, and/or display health parameters of the user. In some embodiments, the user (e.g., a healthcare provider or pregnant female) may manually select which user data to view, for example their own (e.g., pregnant female) or another user (e.g., fetus). The application may display a variety of graphs or other meaningful information (e.g., recommendations, facts, trivia, contact information for services, etc.) to the user, for example a heart rate, stress level, position, and/or activity level. The application may analyze and/or group a variety of health parameters of interest and provide a recommendation to the user, for example sleep more, relax, go for a walk, drink more water, have a glass of cold water, etc. If the one or more parameters of interest indicate a stressed state or a state of distress, the system may send, transmit, or otherwise relay the information to another user of the system, for example a healthcare provider, pediatrician, gynecologist, doula, obstetrician, etc. In some embodiments, the system 100 may automatically contact an emergency service or recommend contacting an emergency service.

In some embodiments, the system 100 and/or application may include different permissions for each user. For example, a user of the system may be able to access his or her data only, all users' data, a subset of all users' data, or any degree of permissions therebetween. The user may sign into the system using one or more credentials (e.g., username, password, security question, etc.), biometrics (e.g., fingerprint, eye scan, face recognition, etc.), or any other user-specific information.

In some embodiments, one or more features of the application are user-specific and/or customizable to the user. For example, a layout, font, color, tone, language, and/or any features of the application are customizable to the user and/or displayed to the user upon the system detecting which user is using the system.

As shown in FIG. 3A, the sensing module 18 further includes a housing 28. The housing 28 functions to store, house, and/or provide a means for integrating one or more sensing module components. The processor 14, memory 16, antenna 24, transmitter, receiver, transceiver, and/or one or more sensors 12 may be disposed in, embedded in, housed in, or otherwise coupled to the housing 28. The housing 28 includes an outer surface for encapsulating, housing, or otherwise storing one or more sensing module components or one or more sensing module components may be embedded in the outer surface of the housing. In some embodiments, the outer surface of the housing may include a first surface (i.e., a user facing surface) 30 opposite a second surface (i.e., an accessory facing surface) 32. In some embodiments, the outer surface further includes an outer perimeter 34. One or more surfaces of the outer surface may be configured for coupling to an accessory worn by or positioned proximate a user, as described elsewhere herein.

The user facing surface 30 and accessory facing surface 32 may be irreversibly fastened together, for example during manufacturing. Alternatively, the user facing surface 30 and accessory facing surface 32 may be reversibly coupled. In some embodiments, the user facing surface 30 and accessory facing surface 32 may be hingedly connected, magnetically coupled, threaded together, snap-fit together, sealed together using one or more screws, or otherwise coupled together. The accessory facing surface 32, user facing surface 30, and/or outer perimeter 34 may include a coupling element and/or be coupleable to an accessory worn by or positionable proximate to a user, as described elsewhere herein.

Figure 3B:
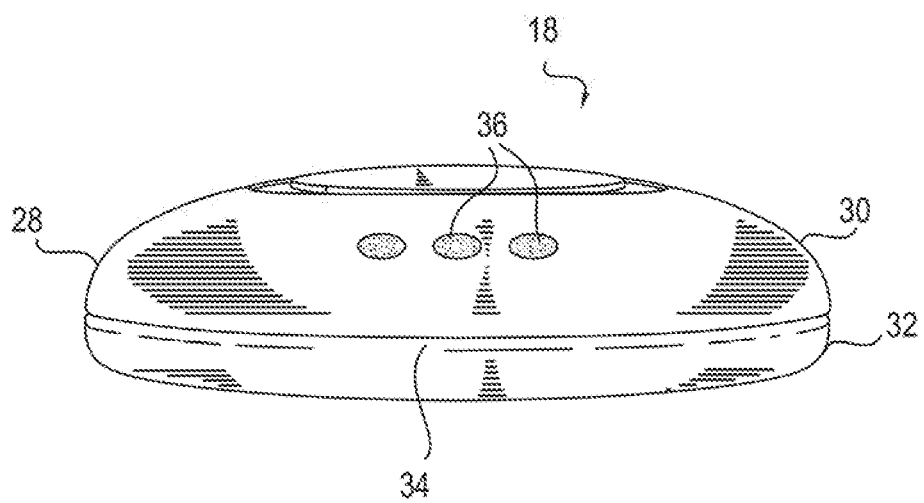
FIG. 3B illustrates one embodiment of a housing comprising one or more indicators.

In some embodiments, an outer surface of the housing 28 includes one or more indicators 36 communicatively coupled to the processor, as shown in FIG. 2C and FIG. 3B. In some embodiments, the one or more indicators 36 are positioned on a user facing surface 30 of the housing 28. In other embodiments, the one or more indicators 36 are positioned on an outer perimeter 34 of the housing 28. The one or more indicators 36 function to indicate a status, setting, or feature of the system. For example, the indicator may include an optical indicator (e.g., light emitting diode (LED), organic LED, fluorescent light, incandescent light, etc.; FIG. 3A), an audible indicator (e.g., speaker relaying a buzz, beep, voice, alarm, etc.), a haptic indicator (e.g., piezoelectric actuator providing vibration), or a display. The indicator may change color, intensity (e.g., light, sound, vibration, etc.), volume, frequency (e.g., flashing light, sound frequency, vibration frequency, etc.), pattern or sequence, or any other adaptation. In some embodiments, two or more indicators are used together to indicate a status, setting, or feature. In some embodiments, the indicator changes based on the type of accessory to which the housing is coupled (e.g., one light indicator for first trimester accessory, two light indicators for second trimester accessory, etc.), which user is using the system (e.g., pink for the mother, blue for the father, yellow for developing fetus), a health status (e.g., health, stresses, distressed, etc.) of the user (e.g., red light indicator for stressed, alarm sounds for stressed, green light indicator for relaxed or healthy, happy music or tune for healthy or relaxed, etc.), a recommendation (e.g., exercise more, drink more water, rest, relax, etc.) to the user (e.g., vibration indicating that recommendation is displayed in application), a wireless network status (e.g., connected to computing device or server or disconnected) (e.g., green for connected, red for disconnected), an update status (e.g., update required, update ready, new update available, up-to-date, etc.), a notification received by the application in the system (e.g., vibration, buzz, ding, beep, etc.), or any other status, feature, or setting.

In some embodiments, as shown in FIGS. 4A-4D, the sensing module 18 further includes an accessory identifier 38 communicatively coupled to the processor. The accessory identifier 38 functions to detect or determine a type of accessory coupled to the sensing module and/or to determine which user is using the system based on the type of accessory detected. For example, the accessory identifier 38 may determine that the sensing module 18 is coupled to a pregnancy patch, and, as such, the user is likely a pregnant female. The accessory identifier 38 is coupled to, positioned on, embedded in, or housed by the housing 28 and coupled to the processor. Upon coupling the housing 28 of the sensing module 18 to the accessory, the processor activates a subset of the plurality of sensors to measure a subset of the plurality of parameters of interest.

In some embodiments, upon coupling the housing 28 of the sensing module 18 to the accessory, the processor configures system parameters to work with the accessory. For example, the processor may activate one or more sensors, an antenna, a receiver, transmitter, transceiver, or other sensing module component. The processor may generate a unique GUI and/or cause the display to display a user-specific interface for displaying one or more parameters of interest.

In some embodiments, the accessory identifier 38 is a plurality of electrical terminals, a mechanical means, optical identifier (e.g., an RGB color sensor that detects a unique printed or LED color associated with the accessory), barcode reader, QR code reader, magnetic strength reader, reed switch, inductive reader (e.g., RFID tag reader, NFC chip reader, etc.), or any other type of reader or identifier.

Figure 4A:
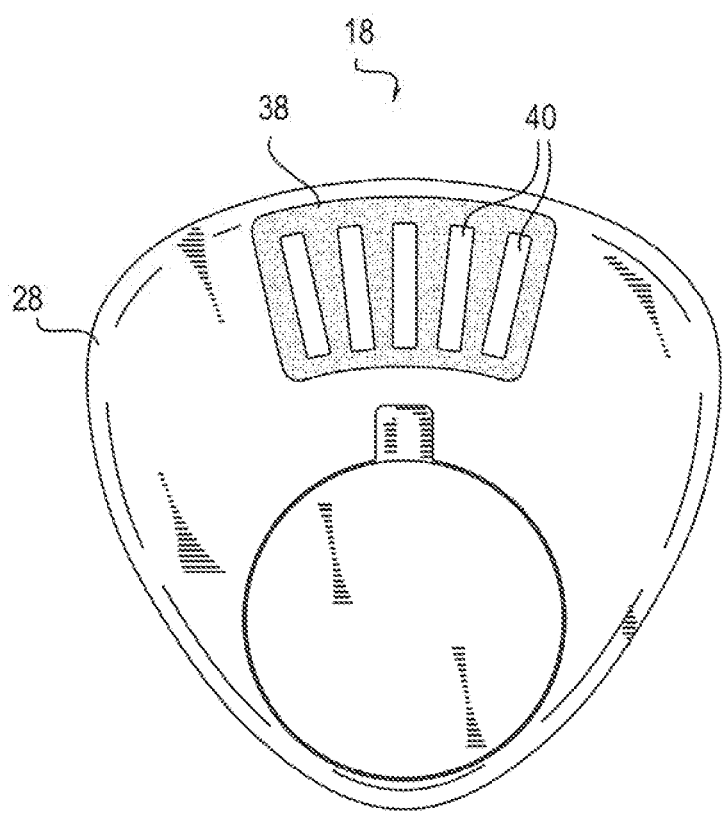
FIG. 4A illustrates one embodiment of a housing comprising an accessory identifier.

In one embodiment, as shown in FIG. 4A, the accessory identifier 38 includes a subset of a plurality of electrical terminals or pins 40 on the housing 28 coupleable to a subset of a plurality of electrical receptacles on the accessory. A unique impedance between the subset of the plurality of electrical receptacles results when connected to the subset of the plurality of electrical terminals 40, enabling detection and identification of the type of accessory coupled to the sensing module 18.

Figure 4B:
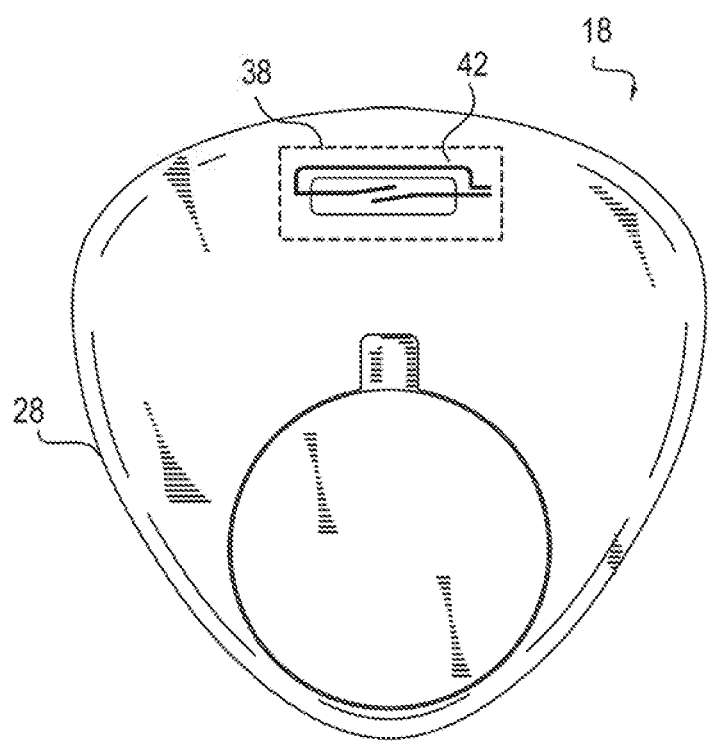
FIG. 4B illustrates one embodiment of a housing comprising an accessory identifier.
Figure 4C:
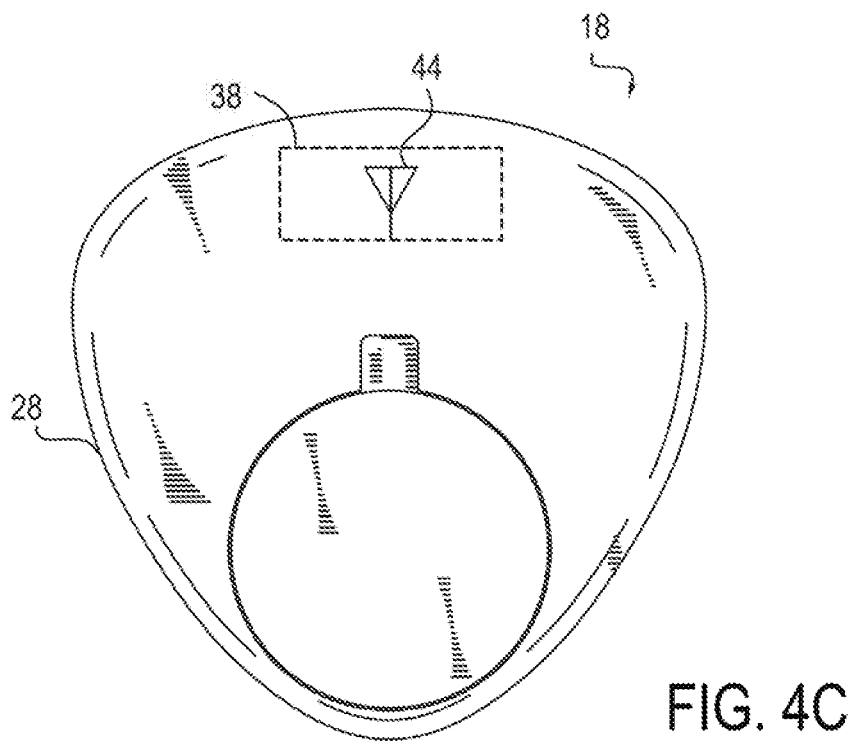
FIG. 4C illustrates one embodiment of a housing comprising an accessory identifier.
Figure 4D:
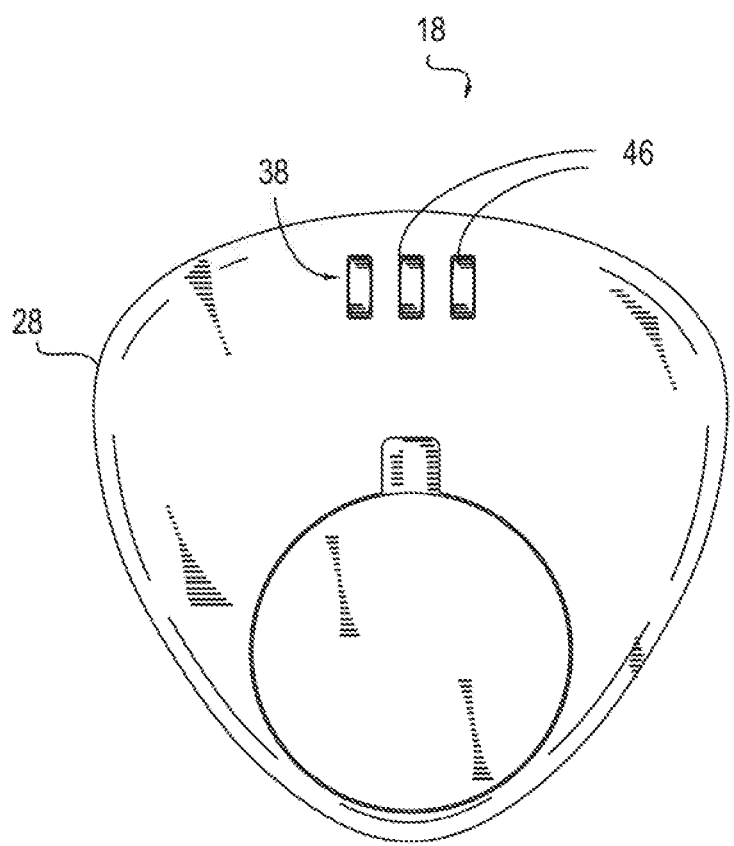
FIG. 4D illustrates one embodiment of a housing comprising an accessory identifier.

In one embodiment, as shown in FIG. 4D, the accessory identifier 38 includes a plurality of grooves, indentations, or receptacles 46 on the housing 28 for receiving a plurality of protrusions on the accessory to identify a type of accessory to which the sensing module 18 is coupled. In one non-limiting example, a wristband may include one protrusion, a bra clip may include two protrusions, and a belly patch may include three protrusions. Each protrusion on the accessory may be unique and/or keyed to a groove or indentation in the housing of the sensing module. In some embodiments, positioning a protrusion on the accessory in a groove or indentation in the housing completes an electrical circuit indicating a type of accessory to which the housing is coupled.

In one embodiment, a magnetic strength reader (e.g., gaussmeter, electromagnetic field meter, magnetometer, etc.) may detect a unique magnetic field (e.g., alternating current electromagnetic field, direct current electromagnetic field, etc.) strength of an accessory to identify the type of the accessory coupled to the housing.

In one embodiment, as shown in FIG. 4B, the accessory identifier 38 includes a plurality of reed switches 42 positioned in or on the housing 28, such that coupling the housing 28 to the accessory (e.g., comprising a magnet) closes a subset of the plurality of reed switches 42, completes the circuit, and indicates a type of accessory to which the housing 28 of the sensing module 18 is coupled.

In one embodiment, as shown in FIG. 4C, the accessory identifier 38 includes an inductive reader or coupler 44 that uses a specific radiofrequency (or other wireless protocol or cellular protocol) to read a tag or label associated with the accessory.

Figure 5A:
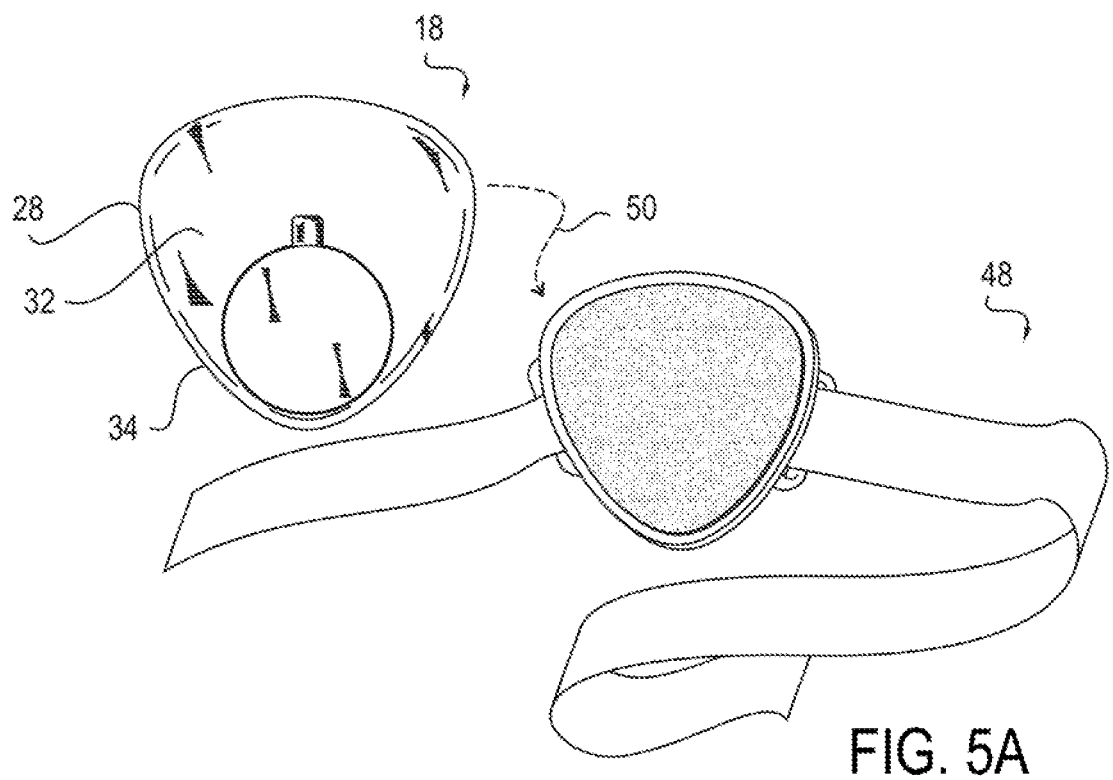
FIG. 5A illustrates one embodiment of a housing comprising a coupling element.
Figure 5B:
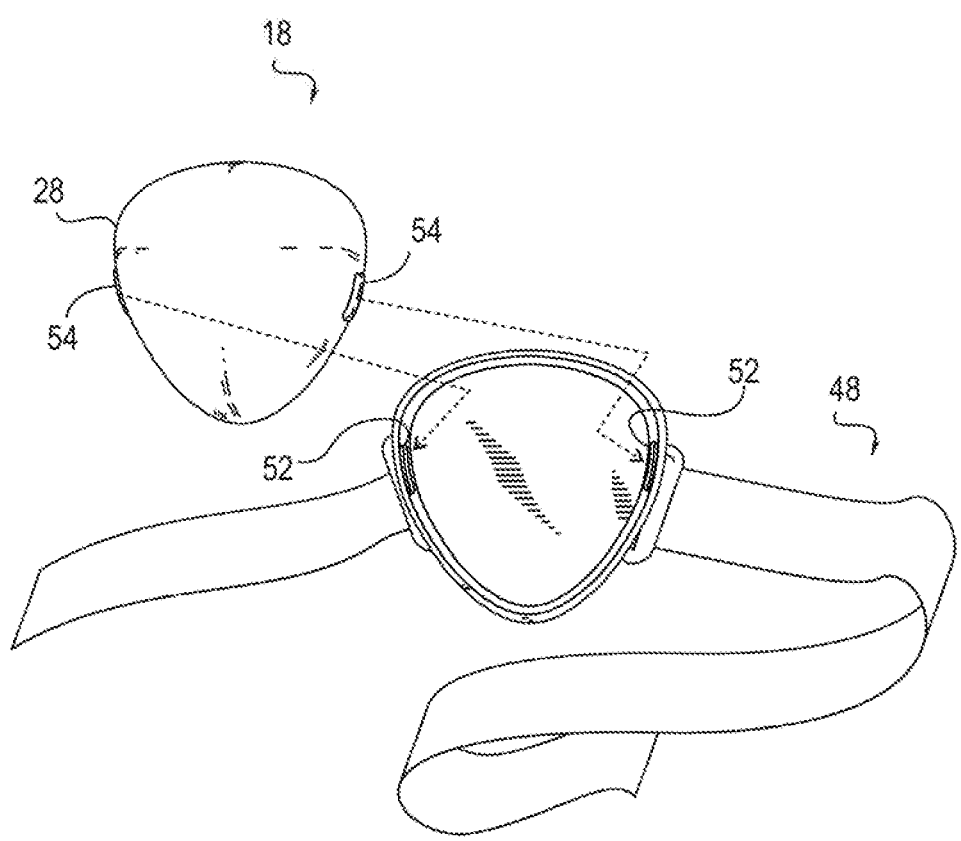
FIG. 5B illustrates one embodiment of a housing comprising a coupling element.
Figure 5C:
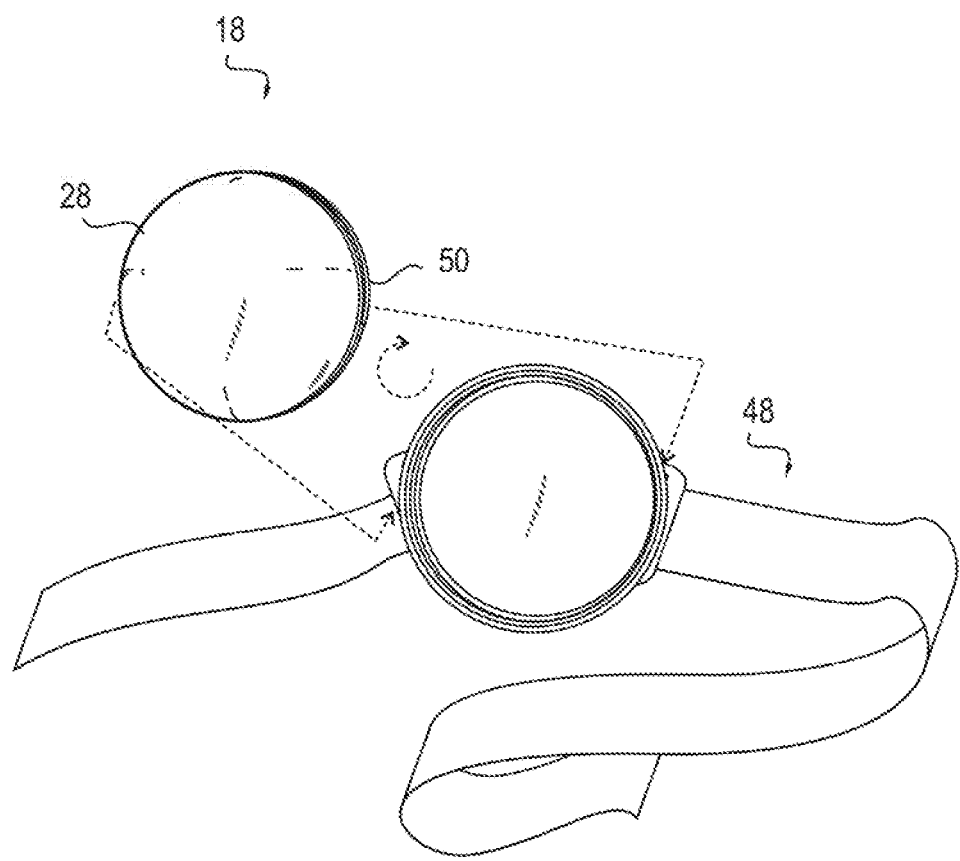
FIG. 5C illustrates one embodiment of a housing comprising a coupling element.

As shown in FIGS. 5A-5C, the housing of the sensing module further includes a coupling element 50. The coupling element 50 functions to secure, fasten, or otherwise couple the housing 28 to an accessory 48 worn by a user or positionable proximate a user. The coupling element 50 is positioned on or embedded in an outer surface of the housing so that the coupling element may couple the housing 28 to the accessory 48. In some embodiments, the coupling element 28 is positioned on an accessory facing surface 32 of the housing 28. In other embodiments, the coupling element 50 is positioned on an outer perimeter 34 of the housing 28. In some variations, as shown in FIG. 5A, the housing 28 includes a permanent magnet and the accessory 48 includes a ferromagnet for coupling the housing 28 to the accessory 48. In some variations, as shown in FIG. 5B, the coupling element comprises a snap fit connection. The housing 28 is snap fit onto the accessory 48. For example, the housing 28 may be sized and shaped to be received by a complementarily sized and shaped receptacle on the accessory 48 or the accessory 48 may include a groove or a series of grooves 52 configured for receiving a protrusion or a series of protrusions 54 extending from the housing 28. In some variations, as shown in FIG. 5C, the coupling element 50 comprises helical grooves complementary to a series of threads. The housing includes threads or a plurality of protrusions and the accessory includes a plurality of grooves for receiving the threads such that the housing is threaded or screwed onto the accessory. In some embodiments, the accessory includes a track or a set of grooves for slidably receiving a coupling element comprising a set of protrusions on the housing.

In some embodiments, the system further includes an accessory 48 or a plurality of accessories. The housing comprising the sensing module is reversibly transitionable between an uncoupled state and a coupled state with the accessory. A few exemplary, non-limiting embodiments of accessories are depicted alone or uncoupled to the housing (e.g., in FIGS. 6A, 7A, 8A, and 9A,) and coupled to the housing (e.g., in FIGS. 6B, 78, 8B, 9B, and 10A-10B). For example, as shown in FIGS. 6A, 7A, 8A, 9A, a base 60 of the accessory is visible in the uncoupled state and, as shown in FIGS. 6B, 7B, 8B, 9B, 10A-10B, the sensing module 18 is visible in the coupled state. The accessory functions to receive or couple to the housing comprising one or more of the sensor(s), processor, and accessory identifier. In some embodiments, the accessory may be a belt, band, clip, clothing item, ring, receptacle, vessel, or holder for receiving a sensing module. The accessory may include an aperture defined by a plurality of sidewalls disposed therein. The plurality of sidewalls defining the aperture of the accessory may be configured to couple to the outer perimeter of the housing or to a perimeter of the user facing surface or the accessory facing surface. In some embodiments, the aperture may further include a base comprising a first side and a second side. The first side of the base is configured for contacting a surface of an accessory and the second side of the base is configured for contacting a skin portion or surface proximate the user.

Figure 6A:
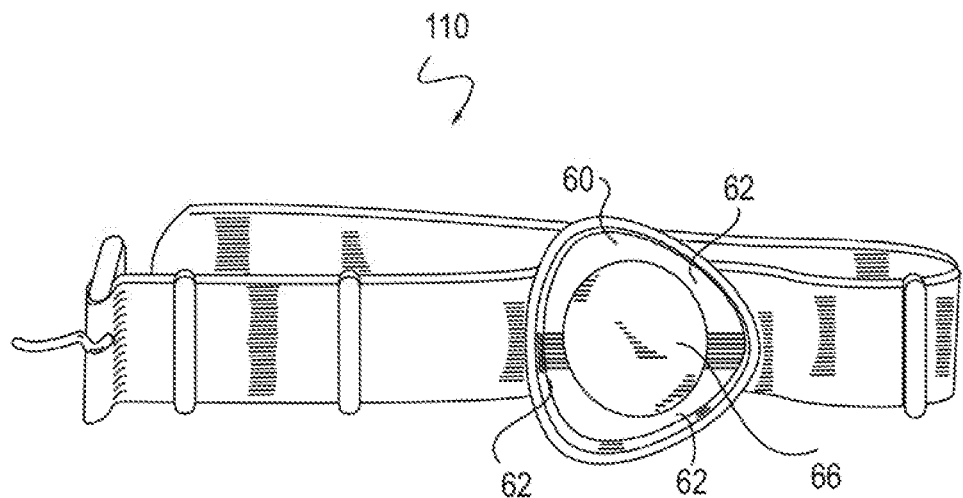
FIG. 6A illustrates one embodiment of an accessory uncoupled from a housing comprising a sensing module.
Figure 7A:
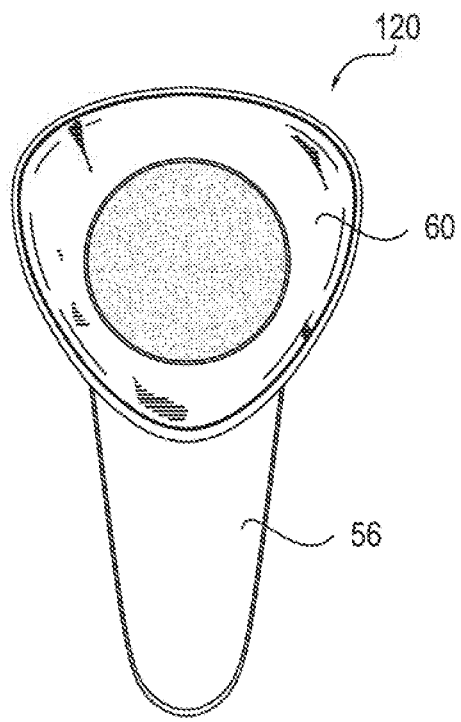
FIG. 7A illustrates one embodiment of an accessory uncoupled from a housing comprising a sensing module.
Figure 8A:
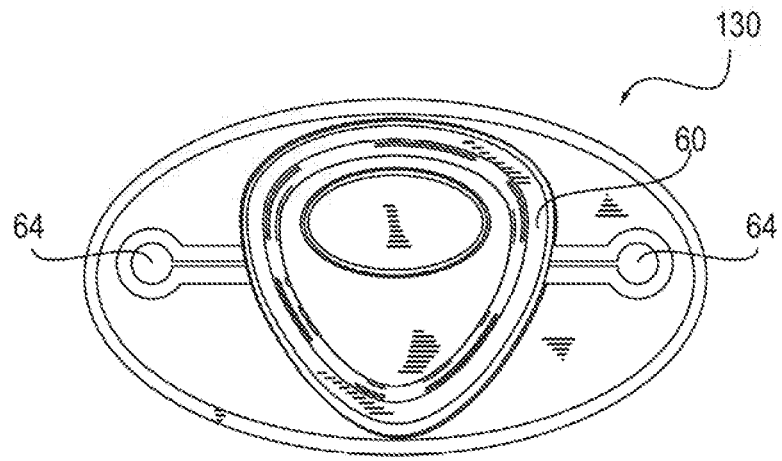
FIG. 8A illustrates one embodiment of an accessory uncoupled from a housing comprising a sensing module.

In some embodiments, as shown in FIG. 6A, the accessory 110 may include a base or receiving element 60 sized, shaped, and configured for matingly receiving at least a portion of the housing. For example, in one non-limiting example, the base 60 includes three side planes 62 and the housing also includes three complementary side planes. In some embodiments, the base 60 further includes one or more electrical contacts 64, for example as shown in FIGS. 8A-8B and 9A-9B, or conductive materials 66, for example as shown in FIG. 6A, for transmitting signals and/or measuring one or more parameters of interest through the base 60 of the accessory. The base 60 may be coupled to a wristband or watchband 110 as shown in FIG. 6A, a bra clip 120 (comprising clip portion 56 for coupling to a bra by a pressure, friction, or force-based mechanism) as shown in FIG. 7A, a belly patch 130 as shown in FIG. 8A and FIG. 9A, or baby clothing, for example a onesie 140 shown in FIG. 10A and a cap or hat 150 shown in FIG. 10B.

In some embodiments, the sensing module, when coupled to the accessory, measures a subset of a plurality of parameters of interest. The subset of the plurality of parameters of interest changes depending on the user and the type of accessory used by the user. Exemplary, non-limiting embodiments of users and accessories before, during, and after pregnancy are shown in Table 1.

TABLE 1

Exemplary, non-limiting embodiments of users and accessories

|  | Pre-Conception | Pregnancy 1st Trimester | Pregnancy 2nd Trimester | Pregnancy 3rd Trimester | Post-Partum |
|---|---|---|---|---|---|
| Father | wristband | N/A | N/A | N/A | wristband |
| Mother | wristband | bra clip | belly patch | belly patch or belt | wristband |
| Fetus | N/A | N/A | belly patch | belly patch or belt | N/A |
| Newborn | N/A | N/A | N/A | N/A | hat, onesie |

Figure 6B:
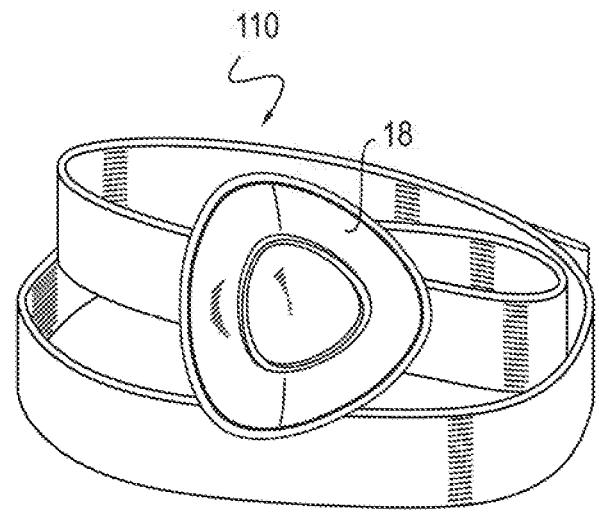
FIG. 6B illustrates one embodiment of an accessory coupled to a housing comprising a sensing module.

In some variations, the sensing module 18, when coupled to the accessory 110, as shown in FIG. 6B, and worn by or positioned proximate a male or female pre-conception, during his partner's pregnancy or during her pregnancy, and/or post-partum, measures one or more health parameters. The health parameters may include, for example: an activity level (e.g., using an accelerometer, gyroscope, pedometer, global positioning device, etc.); sleep quality (e.g., accelerometer, heart rate, heart rate variability); stress level (e.g., bio-impedance, galvanic skin response, ECG, EMG, heart rate, heart rate variability); heart rate (ECG); cardiorespiratory fitness, oxygen saturation level, and/or heart rate variability (e.g., ECG).

Figure 7B:
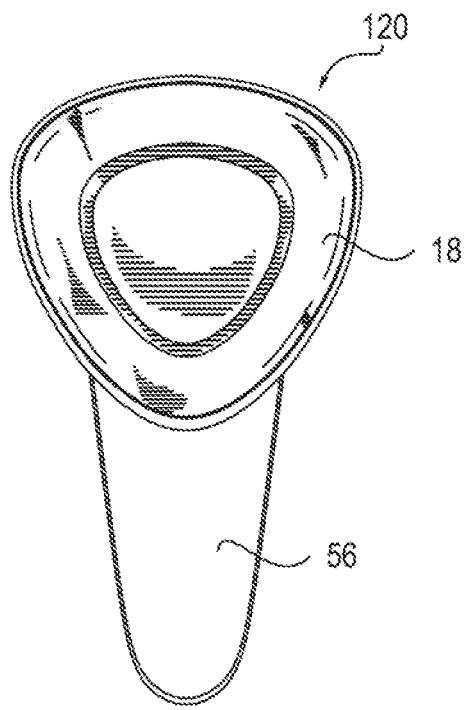
FIG. 7B illustrates one embodiment of an accessory coupled to a housing comprising a sensing module.

In some variations, the sensing module, when coupled to the accessory 120 as shown in FIG. 7B, and worn by or positionable proximate a female pre-conception, during her pregnancy, and/or post-partum, measures an activity level (e.g., using an accelerometer, gyroscope, pedometer, GPS, etc.), sleep quality (e.g., accelerometer, heart rate, heart rate variability), stress level (e.g., bio-impedance, galvanic skin response, ECG, EMG), heart rate (ECG), cardiorespiratory fitness, and/or heart rate variability (e.g., ECG).

Figure 8B:
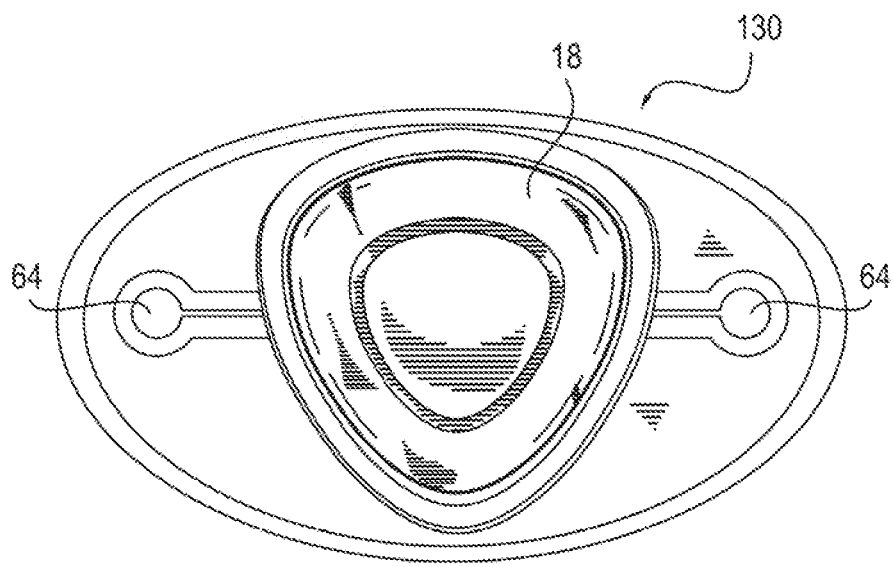
FIG. 8B illustrates one embodiment of an accessory coupled to a housing comprising a sensing module.
Figure 9A:
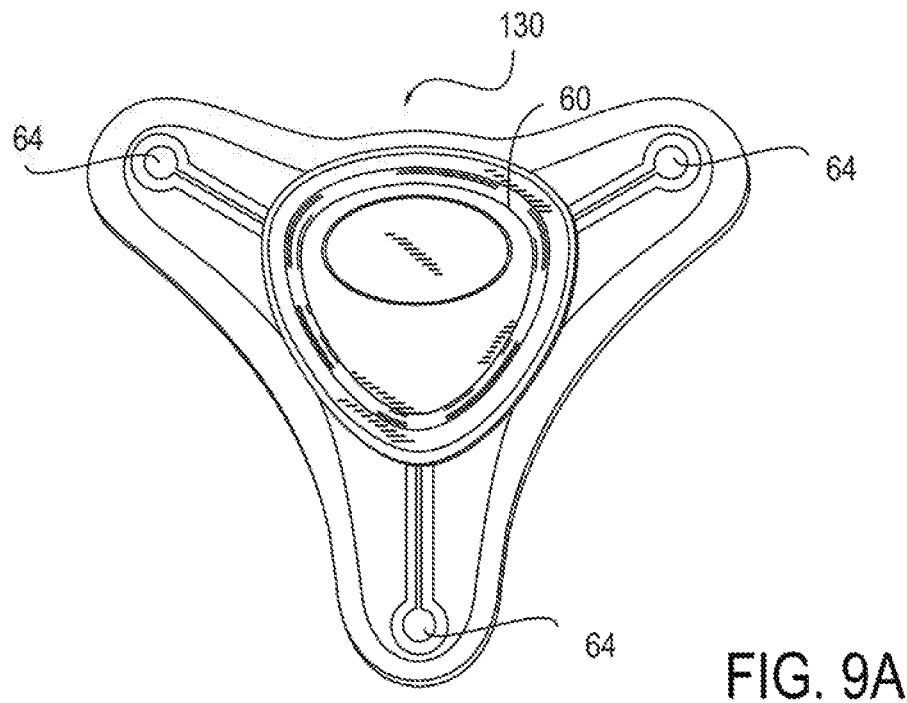
FIG. 9A illustrates one embodiment of an accessory uncoupled from a housing comprising a sensing module.
Figure 9B:
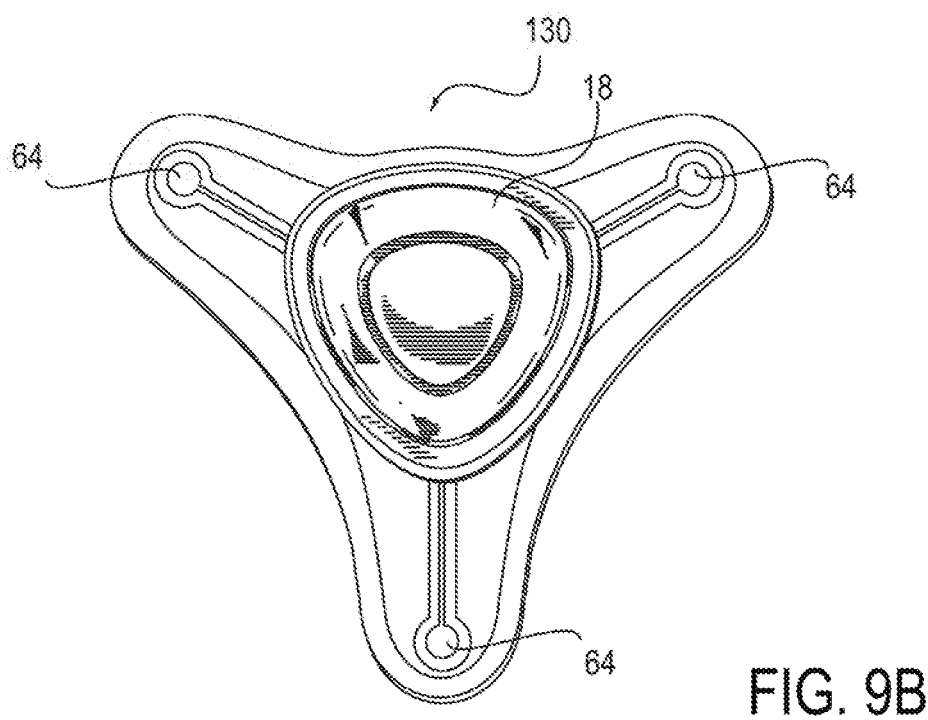
FIG. 9B illustrates one embodiment of an accessory coupled to a housing comprising a sensing module.

In some variations, the sensing module, when coupled to the accessory 130 as shown in FIG. 8B or FIG. 9B, measures a subset of the plurality of parameters of interest of a pregnant female and a subset of the plurality of parameters of interest of a fetus she is carrying. In one non-limiting example, the sensing module, when coupled to a belly patch, measures one or more health parameters of a developing fetus in utero and the expectant mother carrying the developing fetus. In another non-limiting example, a maternal subset of the plurality of parameters of interest may include: an electrohysterography signal (e.g., EHG), maternal uterine activity (e.g., EHG), maternal uterine contractions (e.g., EHG), maternal heart electrical activity (e.g., ECG), maternal heart rate (e.g., ECG), maternal heart rate variability (e.g., ECG), a maternal activity level (e.g., accelerometer, gyroscope, pedometer, global positioning device, etc.), a maternal sleep quality (e.g., accelerometer, ECG), and/or a maternal stress level (e.g., bio-impedance, galvanic skin response, ECG, EMG, respiration). In another non-limiting example, a fetal subset of the plurality of parameters of interest may include: fetal movement (e.g., accelerometer, acoustic sensor, etc.), fetal heart electrical activity (e.g., ECG), fetal heart sound (e.g., Doppler ultrasound, acoustic sensor, etc.), fetal heart rate (e.g., ECG), fetal heart rate variability (e.g., ECG), an amount of amniotic fluid (e.g., bio-impedance, near infra-red spectroscopy), placental oxygenation (e.g., photoplethysmography, near infra-red spectroscopy), placental temperature (e.g., temperature sensor), placental pH (e.g., electrochemical sensor, photoplethysmography, near infra-red spectroscopy), fetal breathing (e.g., Doppler ultrasound), fetal position (e.g., Doppler ultrasound), fetal orientation (e.g., Doppler ultrasound), and/or fetal distress. In some embodiments, a maternal signal is differentiated from a fetal signal, for example, based on location of the signal (e.g., ECG signal close to belly patch may indicate fetal while ECG signal distant from belly patch may indicate maternal), strength of signal (e.g., strong ECG signal with belly patch may indicate fetal while weak ECG signal with belly patch may indicate maternal), frequency or amplitude of signal (e.g., number of heart rate variations in a ten minute period), or any other features or characteristics of the signal.

Figure 10A:
FIG. 10A illustrates one embodiment of an accessory coupled to a housing comprising a sensing module.
Figure 10B:
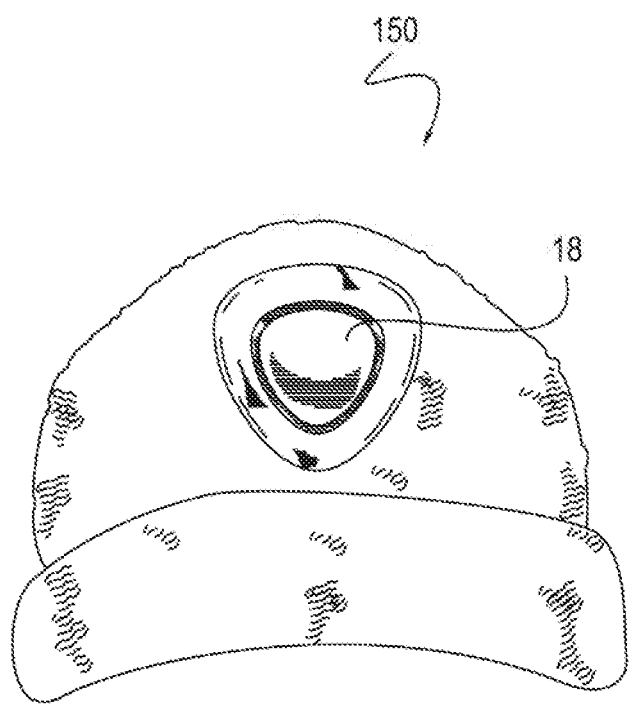
FIG. 10B illustrates one embodiment of an accessory coupled to a housing comprising a sensing module.

In some variations, the plurality of sensors post-partum measures one of: a maternal subset of the plurality of parameters of interest (e.g., using an accessory 110, 120 as shown in FIGS. 6A-6B or FIGS. 7A-7B), a paternal subset of the plurality of parameters of interest (e.g., using an accessory 110 as shown in FIGS. 6A-6B), and a newborn or infant subset of the plurality of parameters of interest (using an accessory 140, 150 as shown in e.g., FIG. 10A or FIG. 10B). In one non-limiting example, a maternal and/or paternal subset of the plurality of parameters of interest includes an activity level, sleep quality, stress level, heart rate, cardiorespiratory fitness, oxygen saturation level, and/or heart rate variability. In another non-limiting embodiment, a newborn or infant subset includes a heart rate (e.g., ECG), heart rate variability (e.g., ECG), blood oxygenation level (e.g., photoplethysmography), breathing rate (e.g., accelerometer, acoustic transducer, photoplethysmography, impedance plethysmography, etc.), movement (e.g., accelerometer, gyroscope, GPS, EMG, etc.), temperature, cries or other vocal sounds (e.g., microphone), and/or brain activity (e.g., EEG).

In some variations, the plurality of sensors measures a patient (e.g., heart rate, stress level, blood pressure, blood flow, blood oxygenation, etc.) and/or a caregiver (e.g., heart rate, stress level, sleep quality, etc.) pre-surgery, during surgery, and/or after surgery, each stage (e.g., pre-surgery, during surgery, post-surgery) having a specific accessory for coupling to the housing comprising the sensing module.

In some variations, the plurality of sensors measures an athlete or individuals in a family before exercising, during exercise, and after exercising. For example, a heart rate, activity level, blood oxygenation level, hydration level, etc. Each stage (e.g., pre-exercise, during exercise, post-exercise) and/or individual has a specific accessory for coupling to the housing comprising the sensing module.

Methods

Figure 11:
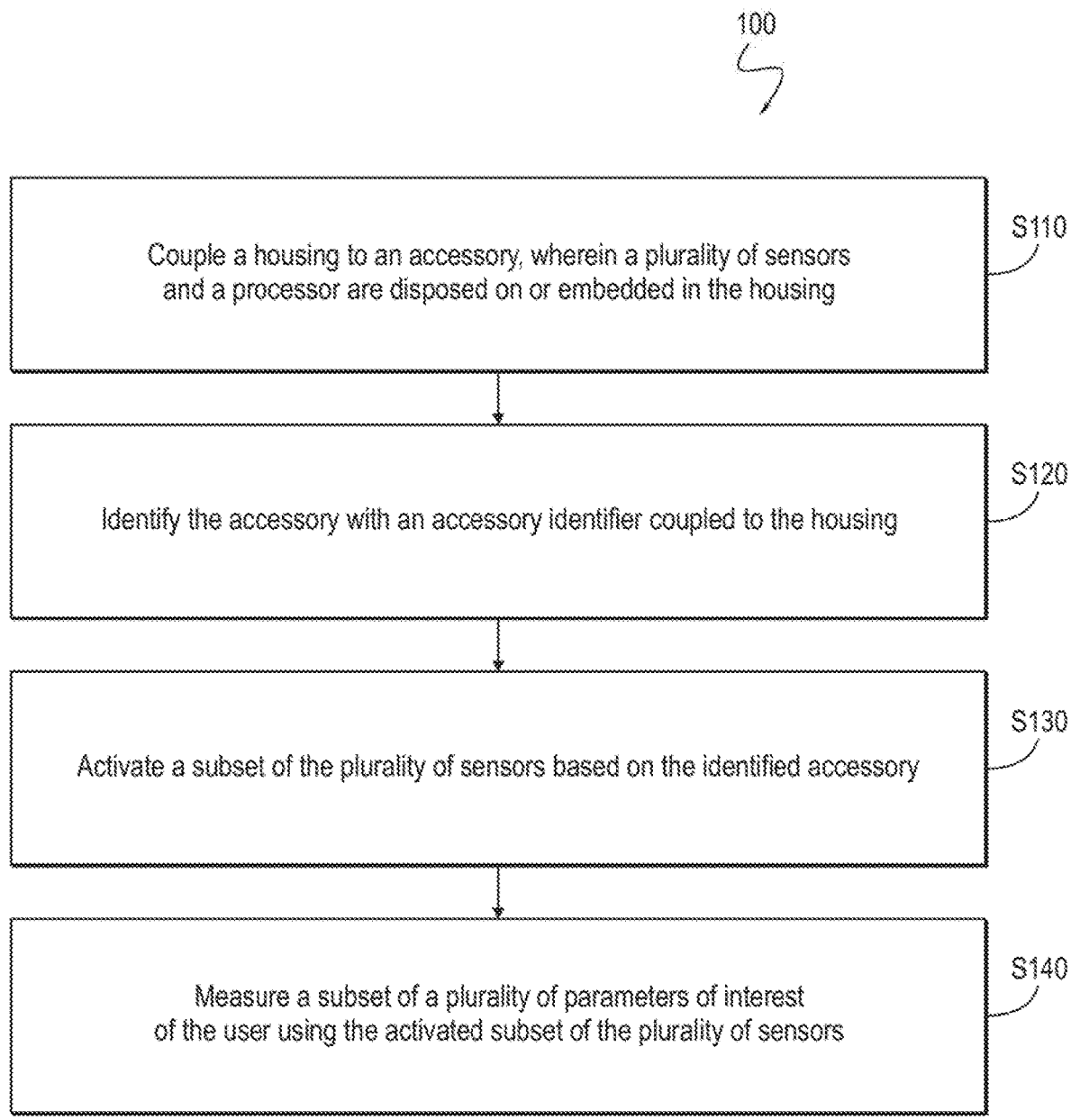
FIG. 11 illustrates one embodiment of a method of using a health monitoring system.

As shown in FIG. 11, one non-limiting example of a method 100 of using a health monitoring system includes coupling a housing to an accessory worn by or positionable proximate a user, wherein a plurality of sensors and a processor are disposed on or embedded in the housing S110; identifying the accessory with an accessory identifier coupled to the housing S120; activating a subset of the plurality of sensors based on the identified accessory S130; and measuring a subset of a plurality of parameters of interest of the user using the activated subset of the plurality of sensors S140. The method functions to customize or tailor sensor or health parameter measurements to a user or a user's interest and preferences based on coupling the sensing module to a specific accessory.

As shown in FIG. 11, one embodiment of a method 100 of using a health monitoring system includes block S110, which recites coupling a housing to an accessory worn by or positionable proximate a user, wherein a plurality of sensors and a processor are disposed on or within the housing. Block S110 functions to couple the system components together so that a type of accessory may be determined and a plurality of parameters of interest may be measured by the system. Coupling may include: screwing or threading the housing onto the accessory, magnetically coupling the housing to the accessory, fastening or snap-fitting the housing to the accessory, or adhering the housing to the accessory. In some embodiments, coupling the housing to the accessory includes turning on one or more system components (e.g., processor, sensors, antenna, etc.) disposed in, embedded in, positioned in or on, or coupled to the housing. In some embodiments, coupling the housing to the accessory includes configuring one or more of these system components.

As shown in FIG. 11, one embodiment of a method 100 of using a health monitoring system includes block S120, which recites identifying the accessory with an accessory identifier coupled to the housing. Block S120 functions to determine which accessory is coupled to the housing. In some embodiments, identifying the accessory includes reading a tag (e.g., RFID tag, NFC tag, barcode, QR code, etc.) associated with the accessory. In some embodiments, identifying the accessory includes determining an impedance or unique impedance signature between two or more electrical receptacles on the accessory. In some embodiments, the step of identifying occurs before coupling (e.g., QR code, barcode, NFC, RFID, etc.), after coupling (e.g., electrical impedance, reed switch, etc.), or substantially at the same time as coupling is occurring.

As shown in FIG. 11, one embodiment of a method 100 of using a health monitoring system includes block S130, which recites activating a subset of the plurality of sensors based on the identified accessory. Block S130 functions to measure a subset of a plurality of parameters of interest based on which user (e.g., mother, father, fetus, newborn, etc.) and/or stage (e.g., pre-conception, pregnancy, post-partum) the user is experiencing. In some embodiments, the step of activating includes accessing user profile data or historical user data or receiving a user input to determine which subset of the plurality of sensors to activate, for example if the user desires to measure fewer parameters than what the accessory allows. In some embodiments, the step of activating occurs automatically upon coupling the housing to the accessory or manually, for example using user input.

As shown in FIG. 11, one embodiment of a method 100 of using a health monitoring system includes block S140, which recites measuring a subset of a plurality of parameters of interest of the user using the activated subset of the plurality of sensors. Block S140 functions to acquire data about user activity, heart health, stress level, position, movement, contractions, etc. to inform the user and/or one or more healthcare providers about a health status of the user.

In some embodiments, the method 100 includes acquiring a plurality of sensor outputs, analyzing the plurality of sensor outputs, and determining a health status of the user. In some embodiments, the step of analyzing includes filtering out noise, artifacts, or other signal variances to decreases the noise-to-sensor signal ratio. In some embodiments, filtering may be used to remove fetal signals from a maternal signal or maternal signals from a fetal signal.

Figure 12:
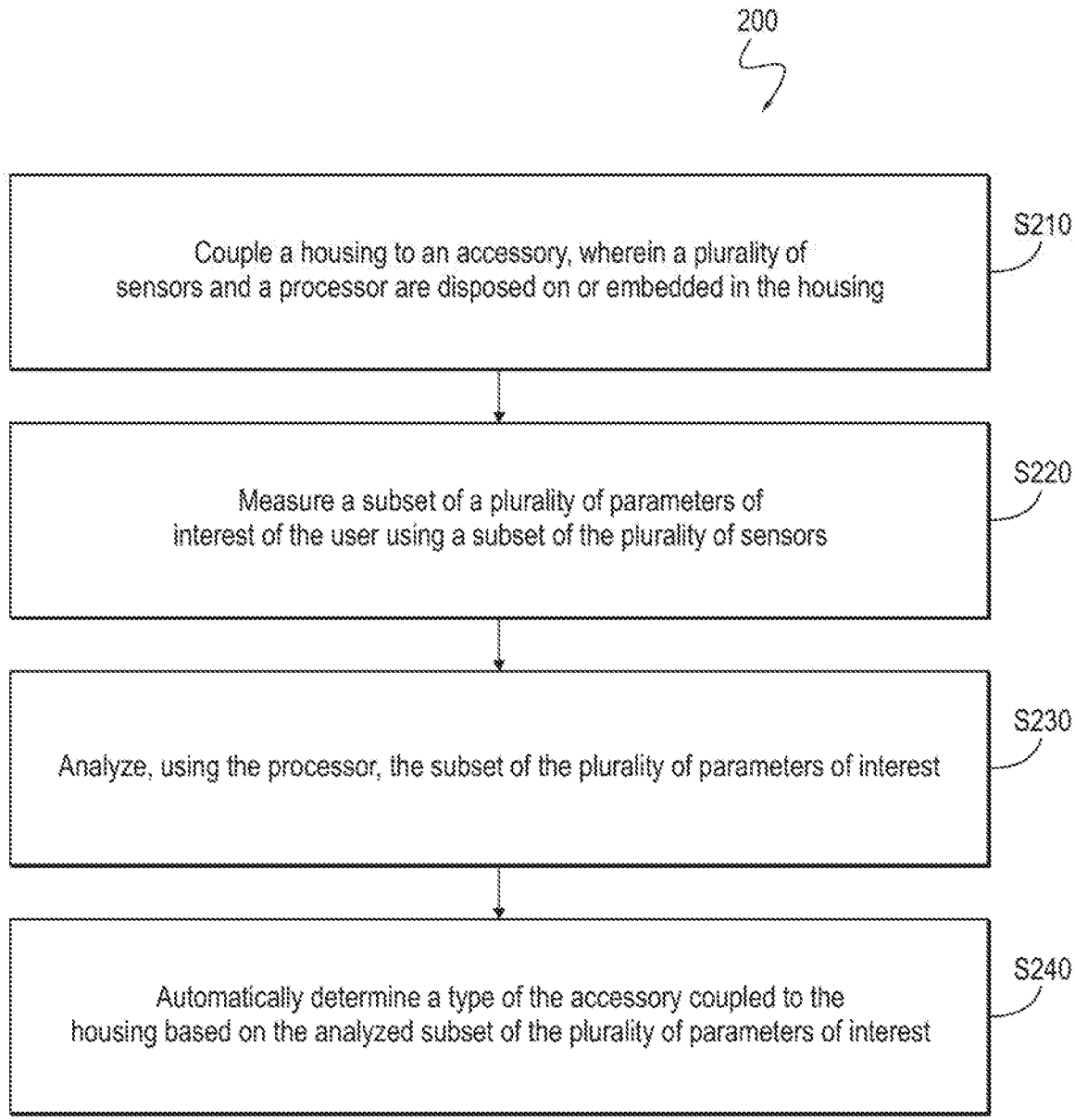
FIG. 12 illustrates one embodiment of a method of using a health monitoring system.

As shown in FIG. 12, one non-limiting example of a method 200 for using a health monitoring system includes coupling a housing to an accessory worn by or positionable proximate to a user, wherein a plurality of sensors and a processor are disposed on or embedded in the housing S210; measuring a subset of a plurality of parameters of interest of the user using a subset of the plurality of sensors S220; analyzing, using the processor, the subset of the plurality of parameters of interest S230; automatically determining a type of the accessory coupled to the housing based on the analyzed subset of the plurality of parameters of interest S240. The method functions to determine which accessory is coupled to the housing by analyzing the data or parameters of interest the plurality of sensors measure.

As shown in FIG. 12, one embodiment of a method 200 of using a health monitoring system includes block S220, which recites measuring a subset of a plurality of parameters of interest of the user using a subset of the plurality of sensors. Block S220 functions to acquire information or data about the user and use that information to determine which accessory the user is using and/or wearing. For example, if a subset of the plurality of sensors measures activity and stress level, the processor may analyze the activity and stress level data and determine that the user is wearing a wristband or watchband accessory. In another example, if a subset of the plurality of sensors measures an amount of amniotic fluid and a pH of the placenta, the processor may analyze these parameters of interest and determine that the user is wearing a third trimester pregnancy patch. In some embodiments, method 200 includes acquiring a plurality of sensor outputs, analyzing the plurality of sensor outputs, and extracting a plurality of parameters of interest from the plurality of sensor outputs. In some embodiments, the method 200 includes displaying the plurality of parameters of interest to the user on a display of a computing device, for example in an application downloaded onto the computing device and/or stored in memory on the computing device. In some embodiments, the method 200 includes comparing the measured subset of the plurality of parameters of interest to a standard set of parameters of interest for each accessory to determine a type of the accessory.

As shown in FIG. 12, one embodiment of a method 200 of using a health monitoring system includes blocks S230 and S240, which recite analyzing, using the processor, the subset of the plurality of parameters of interest; and automatically determining a type of the accessory coupled to the housing based on the analyzed subset of the plurality of parameters of interest. Block S230 functions to determine which subset of all of the plurality of parameters of interest, which could have been measured, were measured. Block S240 functions to determine which accessory is being used by the user, and in some embodiments, the identity of the user using the accessory. In some embodiments, the method 200 includes analyzing a plurality of sensor output signals to determine from which sensor or sensors the plurality of sensor output signals originated.

The above methods may be performed by any suitable monitoring system, such as any of the health monitoring systems described elsewhere herein.

The systems and methods as described herein and variations thereof can be embodied and/or implemented at least in part as a machine configured to receive a computer-readable medium storing computer-readable instructions. The instructions may be executed by computer-executable components integrated with the system and one or more portions of the processor in the sensing module, housing, and/or computing device. The computer-readable medium may be stored on any suitable computer-readable media such as RAMs, ROMs, flash memory, EEPROMs, optical devices (e.g., CD or DVD), hard drives, floppy drives, or any suitable device. The computer-executable component may be a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, system, signal, or parameter.

As used herein, the term "comprising" or "comprises" is intended to mean that the systems and methods include the recited elements, and may additionally include any other elements. "Consisting essentially of" shall mean that the systems and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the systems and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A modular system for monitoring health parameters of a user, the modular system comprising:
   a housing reversibly transitionable between an uncoupled state and a coupled state with an accessory, the housing comprising:
   a plurality of sensors disposed on an outer surface of the housing or within the housing for measuring a plurality of parameters of interest;
   a coupling element positioned on the outer surface of the housing for coupling the housing to the accessory;
   an accessory identifier positioned on or within the housing, wherein the accessory identifier senses a type of accessory when the housing is in the coupled state with the accessory; and
   a processor disposed in the housing and communicatively coupled to the plurality of sensors and the accessory identifier, wherein a method performed by the processor comprises:
   receiving a plurality of sensor outputs from the plurality of sensors;
   analyzing the plurality of sensor outputs from the plurality of sensors;
   automatically determining a type of accessory coupled to the housing based on said analysis and the accessory identifier;
   automatically activating, upon coupling the housing to a specific accessory, a subset of the plurality of sensors based on said determining;
   measuring a subset of the plurality of parameters of interest of the user using the activated subset of the plurality of sensors, wherein the activated subset of the plurality of sensors or the subset of the plurality of parameters of interest are customized to the user based on the coupling of the housing to the specific accessory; and
   processing the subset of the plurality of parameters of interest to extract health related information, wherein the processing comprises analysis of measurements customized to the user.

2. The modular system of claim 1, wherein the subset of the plurality of parameters of interest measured changes based on the type of accessory coupled to the housing.

3. The modular system of claim 1, wherein the accessory identifier comprises a plurality of electrical terminals.

4. The modular system of claim 3, wherein, in the coupled state, the plurality of electrical terminals is connected to a plurality of electrical receptacles on the accessory, and wherein an impedance between the plurality of electrical receptacles is detectable by the accessory identifier.

5. The modular system of claim 1, wherein the accessory is one or more of: wearable by a user and positionable proximate a user.

6. The modular system of claim 1, further comprising an antenna and transceiver communicatively coupled to the processor, wherein the antenna and transceiver wirelessly transmit the subset of the plurality of parameters of interest to a computing device and the wirelessly transmitted subset of the plurality of parameters of interest are customized to the user.

7. The modular system of claim 6, wherein the subset of the plurality of parameters of interest are displayable to a user on a display of the computing device.

8. The modular system of claim 7, wherein a graphical user interface displayed on the display of the computing device adapts based on the type of accessory identified.

9. The modular system of claim 1, wherein the plurality of sensors includes one or more of: a physiological sensor, a bio-potential sensor, an activity sensor, an optical sensor, a bio-impedance sensor, an acoustic sensor, an ultrasound sensor, an electrochemical sensor, a near-infrared spectroscopy sensor, and a temperature sensor.

10. The modular system of claim 9, wherein the paternal subset of the plurality of parameters of interest include one or more of: an activity level, a sleep quality, a stress level, an oxygen saturation level, a cardiorespiratory fitness level, a heart rate, and a heart rate variability.

11. The modular system of claim 9, wherein the maternal subset of the plurality of parameters of interest include one or more of: an activity level, a sleep quality, a stress level, an oxygen saturation level, a cardiorespiratory fitness level, a heart rate, and a heart rate variability.

12. The modular system of claim 1, comprising a set of accessories wherein the set includes two or more of: a wristband, a bra clip, a belt clip, a watchband, an ankleband, a sock, a hat, a first trimester belly patch, a second trimester belly patch, a third trimester belly patch, a pregnancy support belt, a patch coupled to baby clothing, and an accessory integrated into clothing; wherein each accessory is associated with a different user or a different user need, and each user or user need has a set of user specific parameters of interest determined by the coupling of the accessory with the housing comprising the accessory identifier.

13. The modular system of claim 1, wherein during pre-conception, the plurality of sensors measure one of: a paternal subset of the plurality of parameters of interest and a maternal subset of the plurality of parameters of interest, wherein the plurality of sensors are configured to identify the gender of the user, and the modular system is configured to adjust the parameters of interest based on the identified gender.

14. The modular system of claim 1, wherein during pregnancy, the plurality of sensors measures a maternal subset of the plurality of parameters of interest and a fetal subset of the plurality of parameters of interest.

15. The modular system of claim 14, wherein the maternal subset of the plurality of parameters of interest include one or more of: an electrohysterography signal, maternal uterine activity, maternal uterine contractions, maternal heart electrical activity, maternal heart rate, maternal heart rate variability, a maternal activity level, a maternal sleep quality, a maternal oxygen saturation level, a maternal cardiorespiratory fitness level, and a maternal stress level.

16. The modular system of claim 14, wherein the fetal subset of the plurality of parameters of interest include one or more of: fetal movement, fetal heart electrical activity, fetal heart sound, fetal heart rate, fetal heart rate variability, an amount of amniotic fluid, placental oxygenation, placental temperature, placental pH, fetal breathing, fetal position, fetal orientation, and fetal distress.

17. The modular system of claim 1, wherein during post-partum, the plurality of sensors measure one of: a maternal subset of the plurality of parameters of interest, a newborn subset of the plurality of parameters of interest, and a paternal subset of the plurality of parameters of interest.

18. The modular system of claim 17, wherein the maternal subset of the plurality of parameters of interest include one or more of: an activity level, a sleep quality, a stress level, an oxygen saturation level, a cardiorespiratory fitness level, heart rate, and heart rate variability.

19. The modular system of claim 17, wherein the newborn subset of the plurality of parameters of interest include one or more of: a heart rate, heart rate variability, blood oxygenation level, breathing rate, movement, temperature, and vocal sounds.

20. The modular system of claim 17, wherein the paternal subset of the plurality of parameters of interest include one or more of: an activity level, a sleep quality, a stress level, an oxygen saturation level, a cardiorespiratory fitness level, a heart rate, and a heart rate variability.

21. The modular system of claim 1, wherein the modular system is configured for use with a plurality of users and to identify each of the plurality of users based on an identification of the accessory coupled to the housing.

22. A system for measuring health parameters of a user, the system comprising:
a plurality of sensors for measuring a plurality of parameters of interest of a user;
a coupling element for coupling the system to an accessory worn by or positionable proximate the user; and
a processor communicatively coupled to the plurality of sensors,
wherein the processor analyzes a plurality of sensor outputs from the plurality of sensors and automatically determines a type of accessory coupled to the system based on the analyzed plurality of sensor outputs and the sensor or health parameter measurements are customized for the user based on the type of accessory in a way that depends on the coupling element for coupling the system to the accessory worn by the user.

23. The system of claim 22, wherein the plurality of parameters of interest of the user includes one or more of: a maternal activity level, maternal sleep quality, maternal stress level, maternal oxygen saturation level, maternal cardiorespiratory fitness level, maternal heart rate, maternal heart rate variability, maternal electrohysterography signal, maternal uterine activity, maternal uterine contractions, maternal heart electrical activity, paternal activity level, paternal sleep quality, paternal stress level, paternal oxygen saturation level, paternal cardiorespiratory fitness level, paternal heart rate, paternal heart rate variability, paternal heart electrical activity, fetal movement, fetal heart electrical activity, fetal heart sound, fetal heart beat, fetal heart rate, fetal heart rate variability, an amount of amniotic fluid, placental oxygenation, placental temperature, placental pH, fetal breathing, fetal position, fetal orientation, fetal distress, fetal breathing movement, newborn heart rate, newborn blood oxygenation level, newborn breathing rate, newborn movement, newborn temperature, and newborn vocal sounds.

* * * * *